(12) United States Patent
Dreyfus et al.

(10) Patent No.: US 10,836,773 B1
(45) Date of Patent: Nov. 17, 2020

(54) 6-FLUORO-2-METHYLBENZO[D]THIAZOL-5-YL COMPOUNDS

(71) Applicant: Eli Lilly and Company, Indianapolis, IN (US)

(72) Inventors: Nicolas Jacques Francois Dreyfus, Waybridge (GB); Jose Eduardo Lopez, Fishers, IN (US); Leonard Larry Winneroski, Jr., Greenwood, IN (US); Eric Michael Woerly, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/940,504

(22) Filed: Jul. 28, 2020

Related U.S. Application Data

(62) Division of application No. 16/576,080, filed on Sep. 19, 2019, now Pat. No. 10,752,632.

(60) Provisional application No. 62/736,588, filed on Sep. 26, 2018.

(51) Int. Cl.
*C07D 487/04* (2006.01)
*C07D 471/04* (2006.01)

(52) U.S. Cl.
CPC ......... *C07D 487/04* (2013.01); *C07D 471/04* (2013.01)

(58) Field of Classification Search
CPC .................................................... C07D 487/04
See application file for complete search history.

(56) References Cited

U.S. PATENT DOCUMENTS

| | | | |
|---|---|---|---|
| 4,921,887 A | 5/1990 | Matsuo et al. | |
| 9,120,781 B2 | 9/2015 | Li et al. | |
| 10,081,625 B2 | 9/2018 | Dreyfus et al. | |
| 2016/0031871 A1 | 2/2016 | Yu et al. | |
| 2017/0298082 A1 | 10/2017 | Quattropani et al. | |
| 2018/0339984 A1 | 11/2018 | Dreyfus et al. | |

FOREIGN PATENT DOCUMENTS

| | | |
|---|---|---|
| WO | 2005/014579 A1 | 2/2005 |
| WO | 2014/159234 A1 | 10/2014 |
| WO | 2016/030443 A1 | 3/2016 |
| WO | 2017/106254 A1 | 6/2017 |
| WO | 2017/109198 A1 | 6/2017 |
| WO | 2018/109198 A1 | 6/2018 |
| WO | 2018/109202 A1 | 6/2018 |

*Primary Examiner* — Paul V Ward
(74) *Attorney, Agent, or Firm* — Nelsen L Lentz

(57) ABSTRACT

The present invention provides a compound of Formula I:

Formula I

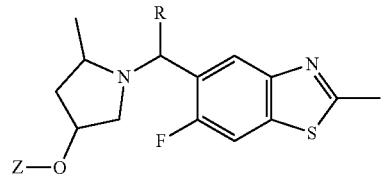

wherein
R is hydrogen or methyl; and
Z is:

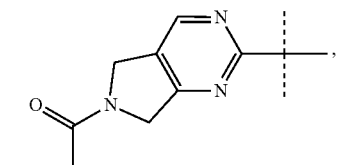

,

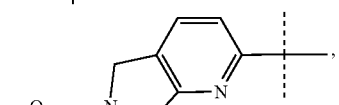

,

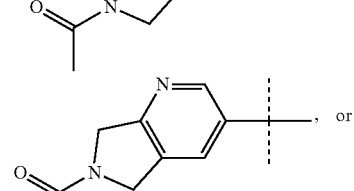

, or

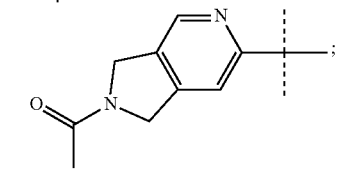

;

or a pharmaceutically acceptable salt thereof, and the use of compounds of Formula I for treating neurodegenerative diseases, such as Alzheimer's disease.

12 Claims, No Drawings

6-FLUORO-2-METHYLBENZO[D]THIAZOL-5-YL COMPOUNDS

The present invention relates to novel 6-fluoro-2-methylbenzo[d]thiazol-5-yl compounds, to pharmaceutical compositions comprising the compounds, to methods of using the compounds to treat neurodegenerative disorders such as Alzheimer's disease (AD), and to intermediates and processes useful in the synthesis of the compounds.

The present invention is in the field of treatment of AD, progressive supranuclear palsy (PSP), and other diseases and disorders involving tau-mediated neurodegeneration, known collectively as tauopathies.

AD is a devastating neurodegenerative disorder that affects millions of patients worldwide. In view of the currently approved agents on the market which afford only transient symptomatic benefits to the patient, there is a significant unmet need in the treatment of AD.

The oligomerization of the microtubule-associated protein tau into filamentous structures such as paired helical filaments (PHFs) and straight or twisted filaments, which give rise to neurofibrillary tangles (NFTs) and neuropil threads (NTs), is one of the defining pathological features of AD and other tauopathies. The number of NFTs in the brains of individuals with AD has been found to correlate closely with the severity of the disease, suggesting tau has a key role in neuronal dysfunction and neurodegeneration (Nelson et al., *J Neuropathol Exp Neurol.*, 71(5), 362-381 (2012)). Tau pathology has been shown to correlate with disease duration in PSP in that cases with a more aggressive disease course have a higher tau burden than cases with a slower progression. (Williams et al., *Brain,* 130, 1566-76 (2007)).

Past studies (Yuzwa et al., *Nat Chem Biol,* 4(8), 483-490 (2008)) support the therapeutic potential of O-GlcNAcase (OGA) inhibitors to limit tau hyperphosphorylation, and aggregation into pathological tau, for the treatment of AD and related tau-mediated neurodegeneration disorders. More recently, the OGA inhibitor Thiamet-G has been linked to slowing motor neuron loss in the JNPL3 tau mouse model (Yuzwa et al., *Nat Chem Biol,* 8, 393-399 (2012)), and to a reduction in tau pathology and dystrophic neurites in the Tg4510 tau mouse model (Graham et al., *Neuropharmacology,* 79, 307-313 (2014)). Accordingly, OGA inhibitors are recognized as a viable therapeutic approach to reduce the accumulation of hyperphosphorylated, pathological forms of tau.

US 2017/0298082 discloses certain glycosidase inhibitors useful in treating tauopathies such as AD. WO 2018/109198 A1 and WO 2018/109202 A1 disclose certain OGA inhibitors useful for treating tauopathies, such as AD and PSP.

OGA inhibitors that are brain penetrant are desired to provide treatments for tau-mediated neurodegeneration disorders, such as AD and PSP. The present invention provides certain novel compounds that are potent inhibitors of OGA. In addition, the present invention provides certain novel compounds that are potent inhibitors of OGA with the potential to be sufficiently brain penetrant to effectively treat tauopathies, such as AD and PSP.

Accordingly, the present invention provides a compound of Formula I:

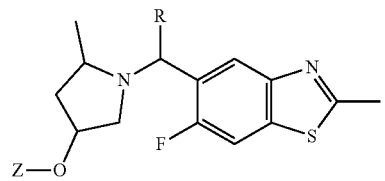

Formula I wherein
R is hydrogen or methyl; and
Z is:

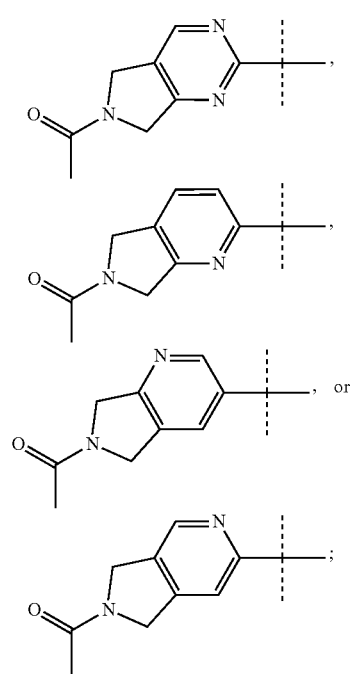

or a pharmaceutically acceptable salt thereof.

The present invention also provides a compound of Formula II:

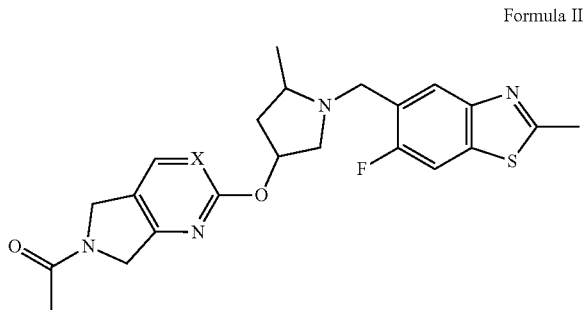

Formula II wherein X is N or CH,
or a pharmaceutically acceptable salt thereof.

The present invention also provides a method of treating Alzheimer's disease in a patient in need of such treatment, comprising administering to the patient an effective amount of a compound of Formula I or II, or a pharmaceutically acceptable salt thereof.

The present invention further provides a method of preventing the progression of mild cognitive impairment to Alzheimer's disease in a patient in need of such treatment, comprising administering to the patient an effective amount of a compound of Formula I or II, or a pharmaceutically acceptable salt thereof.

The present invention also provides a method of treating progressive supranuclear palsy in a patient in need of such treatment, comprising administering to the patient an effective amount of a compound of Formula I or II, or a pharmaceutically acceptable salt thereof. The present invention also provides a method of treating tau-mediated neurodegenerative disorders in a patient, comprising administering to a patient in need of such treatment an effective amount of a compound of Formula I or II, or a pharmaceutically acceptable salt thereof.

Furthermore, this invention provides a compound of Formula I or II, or a pharmaceutically acceptable salt thereof for use in therapy, in particular for use in treating Alzheimer's disease or for use in preventing the progression of mild cognitive impairment to Alzheimer's disease. In addition, this invention provides a compound of Formula I or II, or a pharmaceutically acceptable salt thereof for use in treating progressive supranuclear palsy. The invention also provides a compound of Formula I or II, or a pharmaceutically acceptable salt thereof for use in treating tau-mediated neurodegenerative disorders.

Even furthermore, this invention provides the use of a compound of Formula I or II, or a pharmaceutically acceptable salt thereof, for the manufacture of a medicament for treating Alzheimer's disease or for preventing the progression of mild cognitive impairment to Alzheimer's disease. In addition, this invention provides the use of a compound of Formula I or II, or a pharmaceutically acceptable salt thereof, for the manufacture of a medicament for treating progressive supranuclear palsy. The invention also provides the use of a compound of Formula I or II, or a pharmaceutically acceptable salt thereof, for the manufacture of a medicament for treating tau-mediated neurodegenerative disorders.

The invention further provides a pharmaceutical composition, comprising a compound of Formula I or II, or a pharmaceutically acceptable salt thereof, with one or more pharmaceutically acceptable carriers, diluents, or excipients. The invention further provides a process for preparing a pharmaceutical composition, comprising admixing a compound of Formula I or II, or a pharmaceutically acceptable salt thereof, with one or more pharmaceutically acceptable carriers, diluents, or excipients.

Mild cognitive impairment has been defined as a potential prodromal phase of dementia associated with Alzheimer's disease based on clinical presentation and on progression of patients exhibiting mild cognitive impairment to Alzheimer's disease over time. The term "preventing the progression of mild cognitive impairment to Alzheimer's disease" includes restraining, slowing, stopping, or reversing the progression of mild cognitive impairment to Alzheimer's disease in a patient.

As used herein, the terms "treating" or "to treat" includes restraining, slowing, stopping, or reversing the progression or severity of an existing symptom or disorder.

As used herein, the term "patient" refers to a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be determined by one skilled in the art by the use of known techniques and by observing results obtained under analogous circumstances. In determining the effective amount for a patient, a number of factors are considered, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances. The compounds of the present invention are effective at a dosage per day that falls within the range of about 0.1 to about 15 mg/kg of body weight.

The compounds of the present invention are formulated as pharmaceutical compositions administered by any route which makes the compound bioavailable. Preferably, such compositions are for oral administration. Such pharmaceutical compositions and processes for preparing same are well known in the art (See, e.g., Remington: The Science and Practice of Pharmacy, L. V. Allen, Editor, $22^{nd}$ Edition, Pharmaceutical Press, 2012).

The compounds of Formula I and the pharmaceutically acceptable salts thereof are particularly useful in the treatment methods of the invention, with certain configurations being preferred. The following list of compounds of the present invention describe such configurations. It will be understood that these preferences are applicable both to the treatment methods and to the compounds of the invention.

Compounds of the present invention include:

Formula A

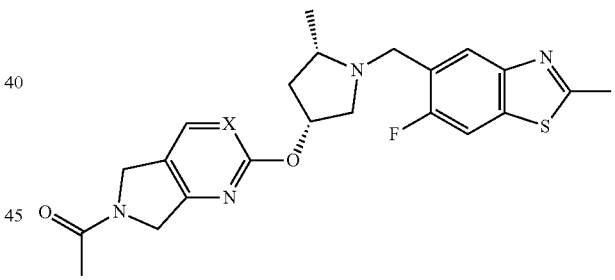

Formula B

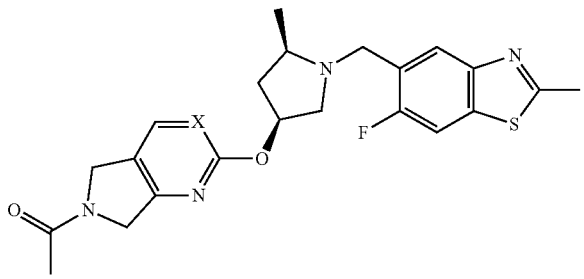

Formula C

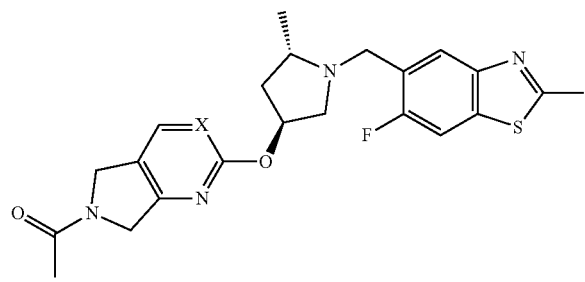

Formula D

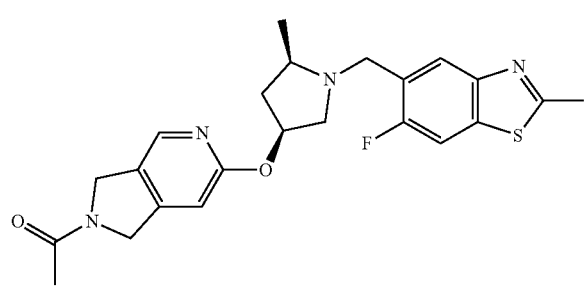

Formula E

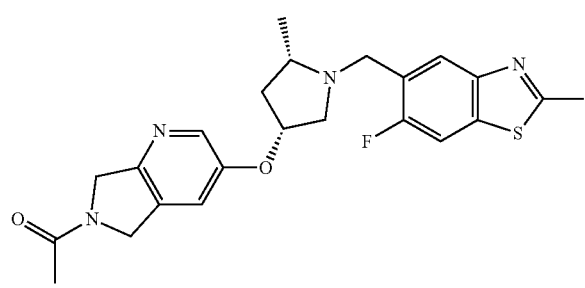

Formula F

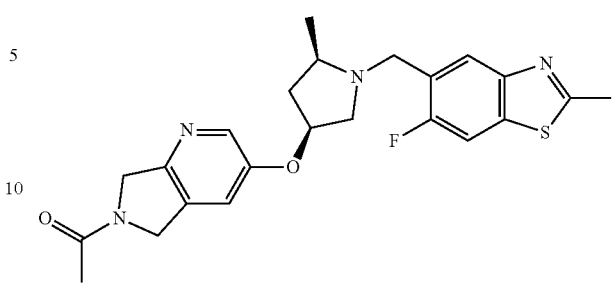

Formula G

Formula H

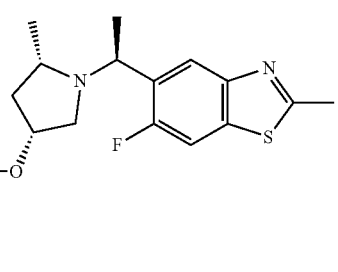

Formula J

Formula K wherein X is N or CH;
and pharmaceutically acceptable salts thereof.

The compound of Formula I wherein the methyl and oxygen substituents on the pyrrolidine ring are in the cis or trans configuration, or pharmaceutically acceptable salt thereof, are included within the scope of the invention, with the cis configuration being preferred. For example, one of ordinary skill in the art will appreciate that the methyl at position 5 on the pyrrolidine ring is in the cis configuration relative to the oxygen at position 3 as shown in Scheme A below:

Scheme A

Formula Ia

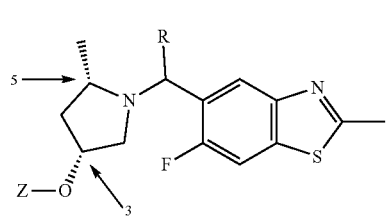

-continued

Formula Ib

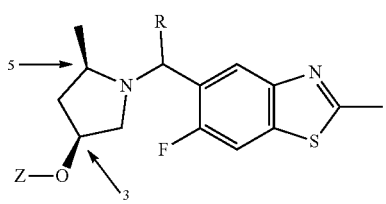

In addition, one of ordinary skill in the art will appreciate that the methyl at position 5 on the pyrrolidine ring is in the trans configuration relative to the oxygen at position 3 as shown in Scheme B below:

Scheme B

Formula Ic

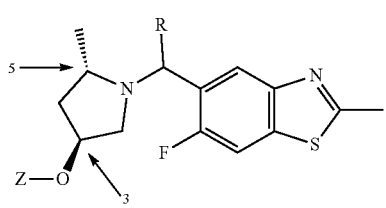

Formula Id

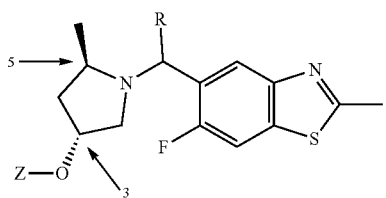

It is preferred that when R is methyl, the methyl group may be in the (R)-configuration or in the (S)-configuration, and it is especially preferred that when R is methyl, the methyl group is in the (S)-configuration.

Although the present invention contemplates all individual enantiomers and diasteromers, as well as mixtures of the enantiomers of said compounds, including racemates, the compound of Formula Ia and pharmaceutically acceptable salts thereof is preferred.

Individual enantiomers may be separated or resolved by one of ordinary skill in the art at any convenient point in the synthesis of compounds of the invention, by methods such as selective crystallization techniques, chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994), or supercritical fluid chromatography (SFC) (See for example, T. A. Berger; "*Supercritical Fluid Chromatography Primer*," Agilent Technologies, July 2015).

A pharmaceutically acceptable salt of the compounds of the invention can be formed, for example, by reaction of an appropriate free base of a compound of the invention and an appropriate pharmaceutically acceptable acid in a suitable solvent under standard conditions well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

The compounds of the present invention, or salts thereof, may be prepared by a variety of procedures known to one of ordinary skill in the art, some of which are illustrated in the schemes, preparations, and examples below. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention. In addition, one of ordinary skill in the art appreciates that compounds of Formula I may be prepared by using starting material or intermediate with the corresponding desired stereochemical configuration which can be prepared by one of skill in the art.

Certain abbreviations are defined as follows: "ACN" refers to acetonitrile; "Ac" refers to acetyl; "AcOH" refers to acetic acid; "Ac$_2$O" refers to acetic anhydride; "BOC" refers to tert-butoxycarbonyl; "CBz" refers to carbonylbenzyloxy; "DCM" refers to methylene chloride or dichloromethane; "DIPEA" refers to diisopropylethylamine; "DMEA" refers to dimethylethylamine; "DMF" refers to N,N-dimethylformamide; "DMSO" refers to dimethyl sulfoxide; "dppf" refers to diphenylphosphinoferrocene; "EDTA" refers to ethylenediaminetetraacetic acid; "ES/MS" refers to Electrospray Mass Spectrometry; "EtOAc" refers to ethyl acetate; "EtOH" refers to ethanol or ethyl alcohol; "h" refers to hour or hours; "IPA" refers to isopropanol or isopropyl alcohol; "JohnPhos" refers to 2-(di-tert-butylphosphino)biphenyl; "KO-t-Bu" refers to potassium-tert-butoxide; "Me" refers to methyl; "min" refers to minute or minutes; "MTBE": refers to methyl tert-butyl ether; "NADP" refers to β-nicotinamide adenine dinucleotide phosphate disodium salt; "NaO-t-Bu" refers to sodium-tert-butoxide; "OAc" refers to acetate or acetoxy; "RT" refers to room temperature; "TEA" refers to triethylamine; "TFA" refers to trifluoroacetic acid; "THF" refers to tetrahydrofuran; "TMEDA" refers to tetramethylethylenediamine; "Tris" refers to tris(hydroxymethyl)aminomethane or 2-amino-2-(hydroxymethyl)propane-1,3-diol; "$[\alpha]_D^{20}$" refers to specific optical rotation at 20° C. and 589 nm, wherein c is the concentration in g/mL.

Scheme 1

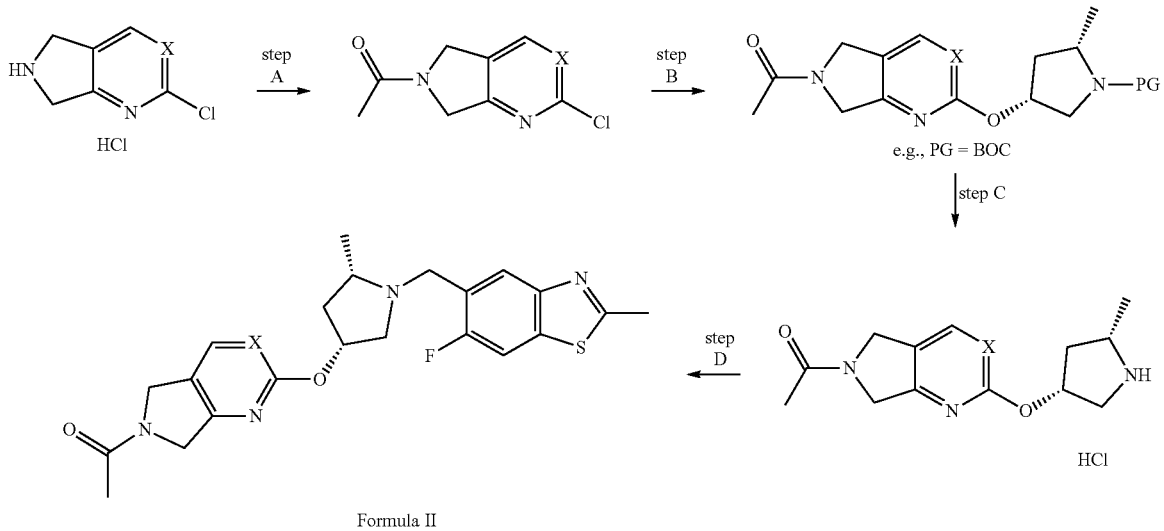

Formula II

Scheme 1 illustrates the synthesis of the compounds of Formula II. In Scheme 1, step A, the pyrrolo-nitrogen of the appropriate 2-chloro-6,7-dihydro-5H-pyrrolopyrimidine hydrochloride (X=N) or 2-chloro-6,7-dihydro-5H-pyrrolopyridine hydrochloride (X=CH) may be acylated under a wide variety of acylating agents well known to the skilled artisan. For example, about 1 equivalent of 2-chloro-6,7-dihydro-5H-pyrrolo[3,4-d]pyrimidine hydrochloride (X=N) or 2-chloro-6,7-dihydro-5H-pyrrolo[3,4-b]pyridine hydrochloride (X=CH) may be dissolved in an appropriate organic solvent, such as DCM, about 4 equivalents of a suitable non-nucleophilic base, such as TEA, pyridine, or DIPEA, may be added, and the mixture may be treated dropwise with the addition of about 1.1 equivalents of acetyl chloride for about 15 to 20 h at RT. The resulting reaction product may be isolated by techniques well known in the art, such as extraction and chromatography. For example, the acylation reaction may be quenched with a suitable mild aqueous base, such as NaHCO$_3$, Cs$_2$CO$_3$, or KHCO$_3$, the resulting biphasic may be extracted with a suitable organic solvent, such as DCM, and the combined organic extracts may be washed sequentially with water, saturated aqueous NaCl, dried over a suitable drying agent, such as Na$_2$SO$_4$ or MgSO$_4$, filtered, and the filtrate may be concentrated under reduced pressure. The resulting residue may be purified by flash chromatography over silica, using a suitable mixture of polar and non-polar organic solvents, such as EtOAc or acetone in hexanes, to obtain the desired acylated product of Scheme 1, step A.

In Scheme 1, step B, nucleophilic aromatic substitution with an appropriately N-protected commercially available hydroxypyrrolidine is well known in the art. The skilled artisan will recognize that a wide array of nucleophilically-stable N-protecting groups may be used, such as Boc, CBz, benzyl, or methyl, as needed for ease of removal. For example, about 1 equivalent of the appropriately N-protected 4-hydroxy-2-methylpyrrolidine may be treated with about 2 equivalents of a suitable strong base, such as NaH, KO-t-Bu, or NaO-t-Bu, in an suitable polar solvent, such as THF, DMF, 1,4-dioxane, or DMSO, at about 0° C. to about RT. About 1.2 equivalents of the desired acylated product of Scheme 1, step A, may be added at about 0° C. to about RT, and the resulting mixture may be stirred at about RT for about 12-24 h. The resulting reaction product may be isolated by techniques well known in the art, such as extraction and chromatography. For example, the reaction mixture may be diluted with water, extracted with an appropriate organic solvent, such as DCM or EtOAc, and the combined organic extracts may be washed sequentially with water, saturated aqueous NaCl, dried over a suitable drying agent, such as Na$_2$SO$_4$ or MgSO$_4$, filtered, and the filtrate may be concentrated under reduced pressure. The resulting residue may be purified by flash chromatography over silica, using a suitable mixture of polar and non-polar organic solvents, such as EtOAc or acetone in hexanes, to obtain the desired product of Scheme 1, step B. The skilled artisan will recognize that different isomers (e.g., cis- or trans-) of the commercially available hydroxypyrrolidine will give different isomers of the product of Scheme 1, step B.

In Scheme 1, step C, the skilled artisan will recognize the removal of the protecting group may be accomplished under an array of conditions well known in the art. For example, wherein PG=BOC, the product of Scheme 1, step B may be dissolved in a suitable organic solvent, such as DCM, and treated with an appropriate acid, such as HCl dissolved in an organic solvent (e.g., Et$_2$O, 1,4-dioxane), or TFA, and the resulting reaction mixture may be stirred at about RT to about 80° C. from about 30 min to 8 h. The resulting reaction product may be isolated by techniques well known in the art, such as evaporation. For example, the reaction mixture may be subjected to concentration under reduced pressure to obtain the HCl salt of the product of Scheme 1, step C.

In Scheme 1, step D, N—C bond formation may be accomplished under a variety of methods well known in the art, including nucleophilic displacement of an alkyl halide, transition-metal catalysis, or under reductive amination conditions. For example, about 1 equivalent of an appropriately substituted aldehyde, such as 6-fluoro-2-methyl-1,3-benzothiazole-5-carbaldehyde and about 1 equivalent of the deprotected pyrrolidine hydrochloride (the product of Scheme 1, step C) may be dissolved in a suitable organic solvent, such as DCM, and the resulting solution may be treated with about 2.5-2.75 equivalents of a non-nucleophilic base, such as DIPEA or TEA for about 30 min to about 1 h. About 3 equivalents of a suitable borohydride reducing agent, such as sodium borohydride, sodium tri(acetoxy) borohydride, or sodium cyanoborohydride, may be added, and the resulting mixture may be stirred at about RT for about 12 to 24 h. The resulting reaction product may be isolated by techniques well known in the art, such as extraction and column chromatography. For example, the reaction mixture may be quenched slowly with a saturated aqueous mild basic solution, such as NaHCO$_3$. The resulting mixture may be extracted with a suitable organic solvent, such as DCM or EtOAc, and the combined organic extracts may be washed sequentially with water, saturated aqueous NaCl, dried over a suitable drying agent, such as Na$_2$SO$_4$ or MgSO$_4$, filtered, and the filtrate may be concentrated under reduced pressure. The resulting residue may be purified by flash chromatography over silica, using a suitable mixture of polar and non-polar organic solvents, such as EtOAc or acetone in hexanes, or methanol in DCM or EtOAc, to obtain the compound of Formula II.

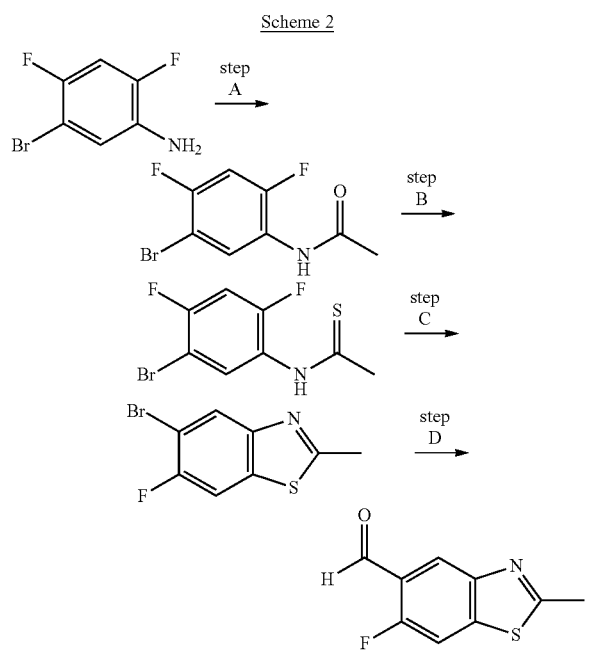

Scheme 2

Scheme 2 illustrates the preparation of the requisite 6-fluoro-2-methyl-1,3-benzothiazole-5-carbaldehyde. In Scheme 2, step A, the skilled artisan will recognize that 5-bromo-2,4-difluoroaniline may be acylated by treatment with a suitable acylating reagent, such as Ac$_2$O or AcCl, at RT and heated to about 60° C., to obtain the acylated aniline. For example, about 1 equivalent of 5-bromo-2,4-difluoroaniline may be added to about 11 equivalents of Ac$_2$O and the resulting mixture may be heated to about 60° C. with stirring for about 10 min. The resulting mixture may be concentrated under reduced pressure, agitated in heptane, and the resulting solid collected by filtration to obtain N-(5-bromo-2,4-difluoro-phenyl)acetamide, the product of Scheme 2, step A.

In Scheme 2, step B, the amide may be converted to the thioamide under a variety of conditions well known in the art, such as with elemental sulfur, Lawesson's Reagent, or ammonium phosphorodithioate, in a suitable organic solvent. More specifically, about 1 equivalent of N-(5-bromo-2,4,-difluoro-phenyl)acetamide may be treated with about 0.5 equivalents of pyridin-1-ium-1-yl-[pyridin-1-ium-1-yl (sulfido)phosphinothioyl]sulfanyl-sulfido-thioxo-phosphane (see, for example, J. Org. Chem. 2011, 76, 1546-1553) in ACN and stirred at 85° C. overnight. The reaction mixture may be concentrated under reduced pressure, the resulting residue dissolved in EtOAc, and the mixture may be washed with saturated aqueous NaCl, dried over Na$_2$SO$_4$, filtered, and the filtrate concentrated under reduced pressure to obtain N-(5-bromo-2,4-difluoro-phenyl)thioacetamide, the product of Scheme 2, step B, as a crude oil, suitable for use without additional purification.

In Scheme 2, step C, one skilled in the art may recognize that N-(5-bromo-2,4-difluoro-phenyl)thioacetamide may be cyclized to the benzothiazole by addition of the appropriate base, such as NaH, Cs$_2$CO$_3$, or NaO-t-Bu, in a polar aprotic solvent such as DMF, DMSO, or ACN. More specifically, about 1 equivalent of thioamide may be treated with a slight excess of NaO-t-Bu in DMF and heated to about 40° C. with stirring overnight. The product may be isolated utilizing extraction techniques as are common to one skilled in the art. For example, the concentrated reaction mixture may be dissolved in EtOAc, washed with H$_2$O and saturated aqueous NaCl, dried over MgSO$_4$, filtered, and concentrated to provide the benzothiazole product of Scheme 2, step C.

In Scheme 2, step D, benzothiazole may undergo carbonylation of the site bearing the bromine as is well described in the art, using an array of palladium catalysts, including PdCl$_2$, Pd(OAc)$_2$, or Pd$_2$(dba)$_3$, ligands including PPh$_3$, PBu$_3$, dppf, or JohnPhos, and carbonyl sources, such as CO, CO/H$_2$, HCOOLi, HCOOK, in a polar aprotic solvent, such as ACN, DMSO, or DMF. More specifically, about 2 equivalents of HCOOK may be added to a reaction mixture containing about 0.05-0.15 equivalents Pd(OAc)$_2$, about 0.05-0.15 equivalents of a suitable phosphine ligand, such as JohnPhos, about 1.2 equivalents 1,1,3,3-tetramethylbutyl isocyanide, and about 1 equivalent 5-bromo-6-fluoro-2-methyl-1,3-benzothiazole dissolved in a suitable polar solvent, such as DMF. The reaction mixture may be heated to about 65° C., stirred overnight, cooled to RT, and the crude aldehyde product of the palladium-mediated reaction may be isolated and purified utilizing techniques well known in the art. For example, the residue may be dissolved in EtOAc, washed sequentially with saturated aqueous Na$_2$CO$_3$ and saturated aqueous NaCl, and purified using silica gel chromatography with a gradient of a mixture of suitable organic solvents, such as heptane:EtOAc, to obtain the desired carbonylated benzothiazole, the product of Scheme 2, step D.

Scheme 3

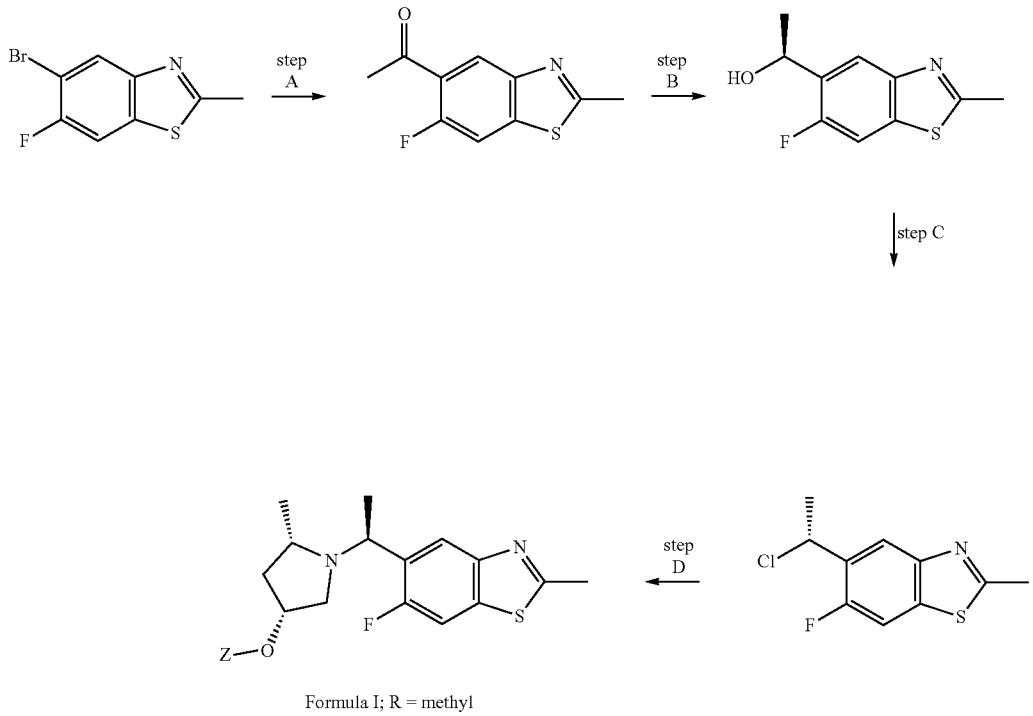

Formula I; R = methyl

In Scheme 3, step A, 5-bromo-6-fluoro-2-methyl-1,3-benzothiazole is combined with about 0.03 equivalents of a suitable palladium catalyst, such as [1,3-bis(diphenylphosphino)propane]palladium (II) dichloride in a suitable solvent, such as ethylene glycol, and about 3 equivalents of trimethylamine under nitrogen. About 5 equivalents of 1-vinyloxybutane are added to the mixture and the reaction is heated at about 100° C. for about 18 hours. After cooling to RT, the reaction is treated with excess aqueous HCl and the product, 1-(6-fluoro-2-methyl-1,3-benzothiazol-5-yl)ethanone, is isolated using standard extraction techniques well know in the art.

In Scheme 3, step B, 1-(6-fluoro-2-methyl-1,3-benzothiazol-5-yl)ethanone is converted to (1S)-1-(6-fluoro-2-methyl-1,3-benzothiazol-5-yl)ethanol using a catalytic amount of (R)-Rucy-xylBinap (CAS #1384974-38-2) and about 0.04 equivalents of potassium tert-butoxide in a suitable solvent, such as toluene, in an autoclave. The autoclave is cooled to about −10° C. and charged to about 450 psi with hydrogen with stirring for about 4.5 hours. The reaction is then warmed to RT and stirred for about 15 hours, then concentrated, and the product of step B is isolated by techniques well known in the art, such as flash chromatography.

In Scheme 3, step C, (S)-1-(6-fluoro-2-methylbenzo[d]thiazol-5-yl)ethan-1-ol is dissolved in a suitable solvent, such as dioxane and treated with about 0.5 equivalents of 1-formylpyrrolidine and about 2.5 equivalents of benzoyl chloride. After stirring for about 36 hours at room temperature, the reaction mixture is cooled to about 0° C., diluted with ethyl acetate and about 1.5 equivalents of N,N-dimethylethylenediamine is added dropwise to the mixture. The mixture is then warmed to RT, added to excess saturated aqueous citric acid solution, and the desired product, 5-[(1R)-1-chloroethyl]-6-fluoro-2-methyl-1,3-benzothiazole, isolated by standard extraction techniques followed by purification via flash chromagraphy.

In Scheme 3, step D, the appropriately substituted pyrrolidine is dissolved in a suitable solvent, such as acetonitrile, treated with about 0.8 equivalents of 5-[(1R)-1-chloroethyl]-6-fluoro-2-methyl-1,3-benzothiazole and excess cesium carbonate, and stirred for about 21 hours at about 68° C. The product of Formula I wherein R is methyl is then isolated and purified under conditions well known in the art.

Scheme 4

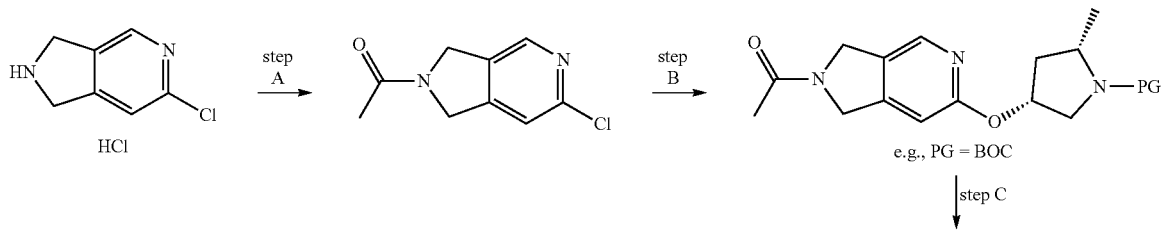

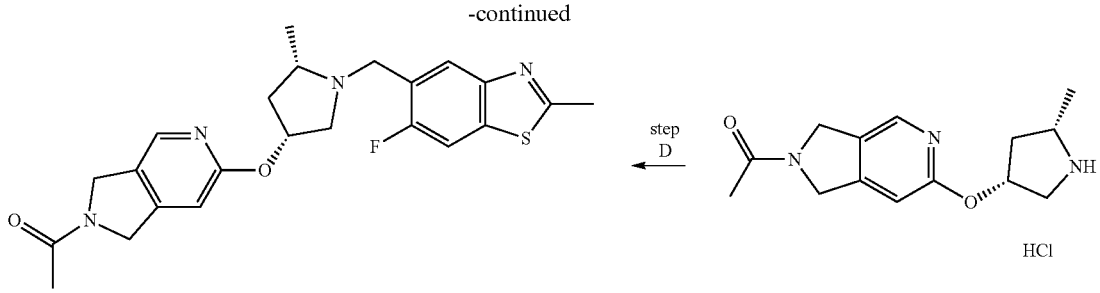

In Scheme 4, steps A through D are carried out in a manner essentially analogous to those described above in Scheme 1, Steps A through D.

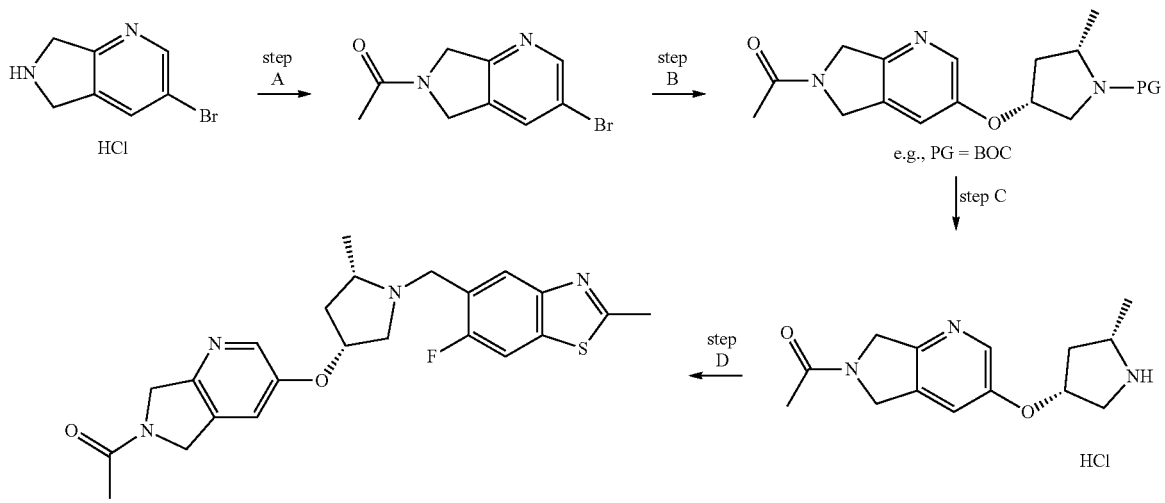

In Scheme 5, steps A through D are carried out in a manner essentially analogous to those described above in Scheme 1, Steps A through D.

PREPARATIONS AND EXAMPLES

The following Preparations and Examples further illustrate the invention and represent typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

LC-ES/MS is performed on an AGILENT® HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C18 2.1×50 mm 3.0 µm; gradient: 5-100% B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: XTERRA® MS C18 columns 2.1×50 mm, 3.5 µm; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM NH₄HCO₃ pH 9; Solvent B: ACN; wavelength: 214 nm.

NMR spectra are performed on a Bruker AVIII HD 400 MHz NMR Spectrometer, obtained as CDCl₃ or DMSO solutions reported in ppm, using residual solvent [CDCl₃, 7.26 ppm; (CD₃)₂SO, 2.05 ppm] as reference standard. When peak multiplicities are reported, the following abbreviations may be used: s (singlet), d (doublet), t (triplet), q (quartet), m (multiplet), br-s (broad singlet), dd (doublet of doublets), dt (doublet of triplets). Coupling constants (J), when reported, are reported in hertz (Hz).

Preparation 1

1-(2-chloro-5,7-dihydro-6H-pyrrolo[3,4-d]pyrimidin-6-yl)ethan-1-one

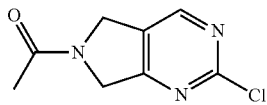

Scheme 1, step A (X=N): To a 0° C. solution of 2-chloro-6,7-dihydro-5H-pyrrolo[3,4-d]pyrimidine HCl (10.4 g, 54.2 mmol) in DCM (250 mL) is dropwise added TEA (37 mL, 265 mmol) and acetyl chloride (5.2 mL, 73 mmol). The reaction mixture is stirred at RT for 19 h. The reaction mixture is diluted with DCM (50 mL) and saturated aqueous NaHCO₃ solution (200 mL). The aqueous layer is extracted with DCM (2×100 mL). The combined organic extracts are washed with saturated aqueous NaCl, dried over MgSO₄, filtered, and concentrated under reduced pressure. The resulting residue is dissolved in DCM, adsorbed onto diatomaceous earth, and purified via flash chromatography over silica gel, eluting with a gradient of 50-100% acetone in hexanes, to obtain the title compound after solvent evaporation of the desired chromatographic fractions (5.17 g, 48% yield). ES/MS m/z: 198 (M+H).

Alternative Procedure for Preparation 1

2-Chloro-6,7-dihydro-5H-pyrrolo[3,4-d]pyrimidine hydrochloride (32.0 g, 167 mmol; see WO17/071636) is ground to a fine powder with a mortar and pestle. The powder is transferred into a flask and DCM (320 mL) and pyridine (35.0 mL, 433 mmol) are added at RT. The reaction mixture is stirred vigorously in an ice-water bath and acetyl chloride (15.5 mL, 217 mmol) is added dropwise over 10 min, maintaining an internal temperature below 10° C. during the addition. The reaction mixture is stirred vigorously at RT for 2 h, then stirred in an ice-water bath, and aqueous 2M HCl solution (320 mL) is added over 5 min, maintaining an internal temperature below 15° C. during the addition. The mixture is stirred at RT for 10 min, and is filtered through a short pad of diatomaceous earth, washing with DCM (50 mL) and water (50 mL). The filtrate is transferred to a separating funnel and the layers are separated. The aqueous layer is extracted with DCM (3×300 mL), and the combined organics are dried over Na₂SO₄ and concentrated under reduced pressure. The resulting residue is suspended in 50% cyclopentyl-methyl ether/heptane (300 mL) and the mixture is stirred vigorously in a 50° C. heating block for 30 minutes. The mixture is stirred at RT for 30 min and is filtered. The filtered solid is dried under vacuum at 40° C. overnight to obtain the title compound (29.38 g, 88% yield) as a pale brown solid. ES/MS m/z: 198 (M+H).

Preparation 2 tert-butyl (2S,4R)-4-((6-acetyl-6,7-dihydro-5H-pyrrolo[3,4-d]pyrimidin-2-yl)oxy)-2-methylpyrrolidine-1-carboxylate

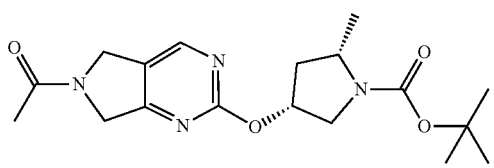 [SMILES: CC(=O)N1Cc2cnc(O[C@@H]3C[C@H](C)N(C(=O)OC(C)(C)C)C3)nc2C1]

Scheme 1, step B (X=N): To a solution of tert-butyl (2S,4R)-4-hydroxy-2-methyl-pyrrolidine-1-carboxylate (2.07 g, 10.3 mmol) and THF (20 mL) at 0° C. is added 60% mass NaH in mineral oil (0.83 g, 20.7 mmol) in one portion and the mixture stirred for 25 min. 1-(2-chloro-5,7-dihydro-6H-pyrrolo[3,4-d]pyrimidin-6-yl)ethan-1-one (2.5 g, 12.7 mmol) and additional THF (5 mL) is added, the mixture is allowed to warm slowly to RT over 45 min, and the mixture is stirred at RT for 19 h. The reaction mixture is diluted with water (75 mL) and EtOAc (75 mL). The aqueous layer is extracted with EtOAc (2×50 mL), and the combined organic extracts are dried over MgSO₄, filtered, and concentrated under reduced pressure. The resulting residue is dissolved in DCM and purified via flash chromatography over silica gel, eluting with a gradient of 50-90% acetone in hexanes, to obtain the title compound after solvent evaporation of the desired chromatographic fractions (3.07 g, 82% yield). ES/MS m/z: 307 (M+H—C₄H₉).

Alternative Procedure for Preparation 2

To a flask is added 60% NaH in mineral oil (5.37 g, 134 mmol) and THF (54 mL) at RT. The flask is stirred in an ice-water bath and a solution of tert-butyl (2S,4R)-4-hydroxy-2-methyl-pyrrolidine-1-carboxylate (13.5 g, 67.1 mmol, see J. Med. Chem. 1988, 31, 1598-1611) in THF (54 mL) is added over 5 min, maintaining an internal temperature below 10° C. during the addition. The reaction mixture is stirred at RT for approximately 15 min and subsequently in a 41° C. heating block for approximately 10 min. To the mixture is added a slurry of 1-(2-chloro-5,7-dihydro-6H-pyrrolo[3,4-d]pyrimidin-6-yl)ethan-1-one (20.1 g, 101 mmol) in THF (297 mL) dropwise with a peristaltic pump over 1 h. The reaction mixture is stirred in a 40° C. heating block overnight, cooled to 0° C. in an ice-water bath, and saturated aqueous NH₄Cl solution (120 mL) is added over 5 min. 2-Methyltetrahydrofuran (10 mL) is added. The mixture is stirred at RT for 5 min, is transferred to a separating funnel, and the layers are separated. The aqueous layer is extracted with 2-methyltetrahydrofuran (130 mL) and the combined organic extracts are dried over Na₂SO₄, filtered, and the filtrate is concentrated under reduced pressure to give the title compound (35.2 g, >99% yield) as a dark red/brown oil. ES/MS m/z: 385 (M+Na).

Preparation 3

1-(2-(((3R,5S)-5-methylpyrrolidin-3-yl)oxy)-5,7-dihydro-6H-pyrrolo[3,4-d]pyrimidin-6-yl)ethan-1-one hydrochloride

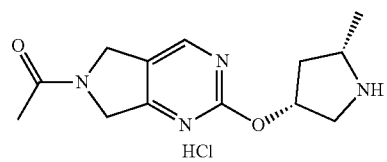 [SMILES: CC(=O)N1Cc2cnc(O[C@H]3CN[C@@H](C)C3)nc2C1 ; Cl]

Scheme 1, step C (X=N): To a solution of tert-butyl (2S,4R)-4-((6-acetyl-6,7-dihydro-5H-pyrrolo[3,4-d]pyrimidin-2-yl)oxy)-2-methylpyrrolidine-1-carboxylate (1.8 g, 5 mmol) in DCM (25 mL) is added a 4M solution of HCl in 1,4-dioxane (6.2 mL, 25 mmol). The resulting mixture is stirred at RT for 4 h. The resulting suspension is concentrated under reduced pressure and the resulting residue is placed under vacuum for 1 h to obtain the title compound (1.48 g, >99% yield). ES/MS m/z: 263 (M+H).

Preparation 4

1-(2-(((3R,5S)-5-methylpyrrolidin-3-yl)oxy)-5,7-dihydro-6H-pyrrolo[3,4-d]pyrimidin-6-yl)ethan-1-one

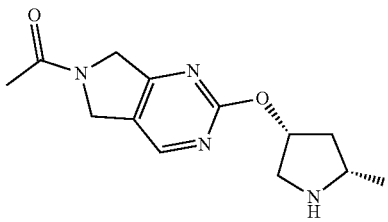 [SMILES: CC(=O)N1Cc2cnc(O[C@H]3CN[C@@H](C)C3)nc2C1]

To a flask is added tert-butyl (2S,4R)-4-[(6-acetyl-5,7-dihydropyrrolo[3,4-d]pyrimidin-2-yl)oxy]-2-methyl-pyrrolidine-1-carboxylate (35.23 g, 67.1 mmol) and isopropyl acetate (176 mL). The reaction mixture is stirred in an ice-water bath (internal temperature 10° C.) and an aqueous 5M solution of HCl (176 mL, 880 mmol) is added dropwise over 5 min, maintaining an internal temperature below 15° C. during the addition. The reaction mixture is stirred at RT for 1 h, the mixture is transferred to a separating funnel with ethyl acetate (5 mL) and water (5 mL), and the layers are separated. The aqueous layer is cooled in an ice-water bath and DCM (180 mL) and water (180 mL) are added. The mixture is stirred vigorously and solid potassium phosphate monohydrate (185 g, 803.37 mmol) is added over 5 min. The mixture is stirred at RT for 5 min, passed through a short pad of diatomaceous earth, washing with DCM (50 mL) and water (50 mL), and the layers are separated. To the aqueous layer is added solid potassium phosphate monohydrate (23.2 g, 101 mmol), the mixture is stirred at RT for 5 min, and the mixture is extracted with DCM (3×180 mL). The combined organics are dried over $Na_2SO_4$ and concentrated under reduced pressure to give the title compound (18.23 g, 67% yield) as a brown foamy solid. ES/MS m/z: 263 (M+H).

Preparation 5

1-(2-chloro-5,7-dihydro-6H-pyrrolo[3,4-b]pyridin-6-yl)ethan-1-one

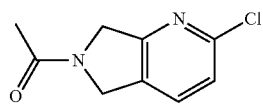

Scheme 1, step A (X=CH): To a 0° C. solution of 2-chloro-6,7-dihydro-5H-pyrrolo[3,4-b]pyridine hydrochloride (1.0 g, 5.2 mmol) in DCM (13 mL) is dropwise added DIPEA (3.6 mL, 21 mmol) and acetyl chloride (0.4 mL, 6 mmol). The reaction mixture is stirred at RT for 24 h. The resulting mixture is diluted with DCM (20 mL) and saturated aqueous $NaHCO_3$ (30 mL). The aqueous layer is extracted with DCM (2×30 mL). The combined organic extracts are dried over $MgSO_4$, filtered, and concentrated under reduced pressure. The resulting residue is dissolved in DCM, adsorbed onto diatomaceous earth, and purified via flash chromatography over silica gel, eluting with a gradient of 50-100% acetone in hexanes, to obtain the title compound after solvent evaporation of the desired chromatographic fractions (0.95 g, 92% yield). ES/MS m/z: 197 (M+H).

Preparation 6 tert-butyl (2S,4R)-4-((6-acetyl-6,7-dihydro-5H-pyrrolo[3,4-b]pyridin-2-yl)oxy)-2-methylpyrrolidine-1-carboxylate

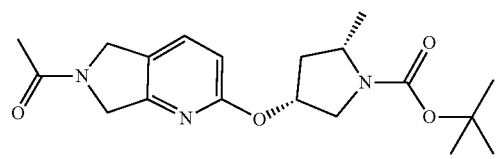 [SMILES: CC(=O)N1Cc2ccc(O[C@@H]3C[C@H](C)N(C(=O)OC(C)(C)C)C3)nc2C1]

Scheme 1, step B (X=CH): To a solution of tert-butyl (2S,4R)-4-hydroxy-2-methyl-pyrrolidine-1-carboxylate (0.41 g, 2.03 mmol), 1-(2-chloro-5,7-dihydro-6H-pyrrolo[3,4-b]pyridin-6-yl)ethan-1-one (0.47 g, 2.36 mmol), and THF (8 mL) at RT is portion wise added KO-t-Bu (0.45 g, 4 mmol) and the mixture is stirred at 50° C. for 4.5 h. The reaction mixture is diluted with water (50 mL) and EtOAc (50 mL). The aqueous layer is extracted with EtOAc (2×50 mL), and the combined organic extracts are dried over $MgSO_4$, filtered, and concentrated under reduced pressure. The resulting residue is dissolved in DCM and purified via flash chromatography over silica gel, eluting with a gradient of 40-100% acetone in hexanes, to obtain the title compound after solvent evaporation of the desired chromatographic fractions (0.34 g, 47% yield). ES/MS m/z: 262 (M+H—$C_4H_9$).

Preparation 7

1-(2-(((3R,5S)-5-methylpyrrolidin-3-yl)oxy)-5,7-dihydro-6H-pyrrolo[3,4-b]pyridin-6-yl)ethan-1-one hydrochloride

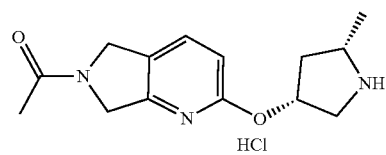 [SMILES: CC(=O)N1Cc2ccc(O[C@H]3CN[C@@H](C)C3)nc2C1 ; Cl]

Scheme 1, step C (X=CH): To a solution of tert-butyl (2S,4R)-4-((6-acetyl-6,7-dihydro-5H-pyrrolo[3,4-b]pyridin-2-yl)oxy)-2-methylpyrrolidine-1-carboxylate (0.34 g, 0.94 mmol) in DCM (5.0 mL) is added a 4M solution of HCl in 1,4-dioxane (1.2 mL, 4.8 mmol). The resulting mixture is stirred at RT for 3 h. The resulting suspension is concentrated under reduced pressure, and the resulting residue is placed under vacuum for 1 h to obtain the title compound (0.28 g, >99% yield). ES/MS m/z: 262 (M+H).

Preparation 8

N-(5-bromo-2,4-difluoro-phenyl)acetamide

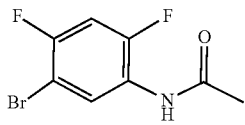

Scheme 2, step A: To a flask is added Ac$_2$O (389 mL) with stirring in a heating block at about 61° C. (internal temperature 60° C.). To the flask is added 5-bromo-2,4-difluoroaniline (77.7 g, 374 mmol) portion wise over 30 min, maintaining an internal temperature below 65° C. during the addition. The reaction mixture is stirred in a heating block at about 61° C. for 10 min, and cooled to RT to give a residue which is concentrated from toluene (4×200 mL) to give a pale brown/pink solid. The concentrated solid is suspended in heptane (80 mL) and the mixture is agitated on a rotary evaporator in a 50° C. water bath for 15 min at atmospheric pressure, cooled to RT, and filtered. The filtered solid is collected and dried under vacuum at 40° C. for 2 h to obtain the title compound (89.6 g, 95% yield) as an off-white solid. ES/MS m/z: 250 (M+H).

Preparation 9

N-(5-bromo-2,4-difluoro-phenyl)thioacetamide

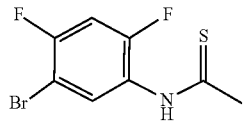

Scheme 2, step B: To a solution of N-(5-bromo-2,4-difluoro-phenyl)acetamide (89.6 g, 358 mmol) in anhydrous ACN (896 mL) is added pyridin-1-ium-1-yl-[pyridin-1-ium-1-yl(sulfido)phosphinothioyl]sulfanyl-sulfido-thioxo-phosphane (68.2 g, 179 mmol, J. Org. Chem. 2011, 76, 1546-1553) at RT. The slurry is stirred in a 85° C. heating block overnight (internal temperature 80° C.), cooled to RT, and poured into a mixture of ice (200 g) and saturated aqueous NaCl (700 mL). The mixture is diluted with EtOAc (900 mL) stirred at RT for 10 min, the layers are separated, and the aqueous layer additionally extracted with EtOAc (900 mL). The combined organic extracts are washed with saturated aqueous NaCl solution (900 mL), dried over Na$_2$SO$_4$, and concentrated under reduced pressure to give the title compound as a dark brown oil, which is dissolved in DMF (953 mL) at RT, and used without additional purification.

Preparation 10

5-bromo-6-fluoro-2-methyl-1,3-benzothiazole

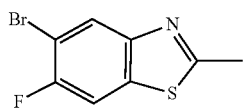

Scheme 2, step C: To a DMF solution of N-(5-bromo-2,4-difluoro-phenyl)thioacetamide is added NaO-t-Bu (42.6 g, 430 mmol) portion wise over 20 min with stirring, maintaining an internal temperature below 30° C. The reaction mixture is stirred at RT for 5 min, stirred overnight in a 42° C. heating block (internal temperature 40° C.), and cooled to RT. The reaction mixture is added dropwise to a mixture of ice (250 g) and H$_2$O (700 mL) over 5 min, maintaining an internal temperature below 20° C. The mixture is stirred at RT for 10 min and filtered. The filtered solid is dried under vacuum at 40° C. overnight, and suspended in 50% MeOH/H$_2$O (480 mL). The mixture is stirred in a 45° C. heating block for 15 min, cooled to RT, and filtered. The filtered solid is dried under vacuum at 40° C. for 72 h to give a pale brown solid. The material is combined with EtOAc (700 mL) and the mixture is stirred at RT for 10 min, H$_2$O (700 mL) is added, and the layers separated. The aqueous layer is extracted with EtOAc (700 mL), then the combined organic extracts are washed with saturated aqueous NaCl (700 mL), dried over MgSO$_4$, and concentrated under reduced pressure to give the title compound (62.7 g, 71% yield) as a brown solid. $^1$H NMR (d$_6$-DMSO) δ: 2.82 (s, 3H), 7.57 (m, 1H), 8.12 (m, 1H).

Preparation 11

6-fluoro-2-methyl-1,3-benzothiazole-5-carbaldehyde

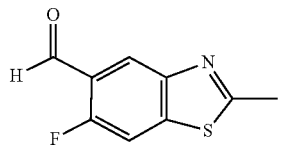

Scheme 2, step D: 5-bromo-6-fluoro-2-methyl-1,3-benzothiazole (100.9 g, 410 mmol) in DMF (1009 mL) is sparged with N$_2$ for 5 min at RT with stirring. Potassium formate (52.3 g, 615.0 mmol), palladium(II) acetate (2.82 g, 12.30 mmol), 2-(di-tert-butylphosphino)biphenyl (5.19 g, 17.2 mmol) and 1,1,3,3-tetramethylbutyl isocyanide (90.8 mL, 492.0 mmol) are added and the mixture is sparged with N$_2$ for 30 min at RT with stirring. The reaction mixture is stirred overnight at an internal temperature of 65° C., cooled to 20-25° C., and 2M aqueous HCl solution (820 mL) is added dropwise over 30 min, maintaining an internal temperature below 30° C. The resulting mixture is stirred at 20-25° C. for 2 h and diluted with EtOAc (1.5 L) and H$_2$O (1 L). The layers are separated and the organic layer is washed with 10% aqueous N-acetyl-cysteine solution (2×1 L), saturated aqueous Na$_2$CO$_3$ (750 mL×2) and saturated aqueous NaCl (750 mL); the organic extract is dried over MgSO$_4$ and concentrated under reduced pressure to provide the first batch of crude material. The aqueous HCl layer from the first extraction is further extracted with EtOAc (1 L, then 500 mL), and the combined organic extracts are washed with saturated aqueous NaCl (500 mL), dried over MgSO₄, and concentrated under reduced pressure to provide the second batch of crude material. The combined aqueous N-acetylcysteine layers are then extracted with EtOAc (1 L, then 500 mL) and the combined organic extracts are washed sequentially with saturated aqueous Na₂CO₃ (500 mL) and saturated aqueous NaCl (500 mL); the combined organic extracts are dried over MgSO₄ and concentrated under reduced pressure to provide the third batch of crude material. The three batches of crude material are combined in MTBE (250 mL) and heptane (250 mL) and the resulting slurry is stirred at RT for 20 min. The resulting precipitate is filtered and washed with heptane (250 mL). The filtered solid is dried under vacuum at 45° C. to give a first batch of product. The filtrate is concentrated and the residue is purified by column chromatography over silica, eluting with a gradient of 0-100% EtOAc/heptane. The product-containing fractions are combined and concentrated to a volume of approximately 400 mL, the resulting slurry is stirred at RT for 15 min, filtered, and the filtered solid is washed with heptane (200 mL), to give a second batch of product. The first and second batches of product are combined with heptane (500 mL), slurried at RT, filtered, and the filtered solid is washed with heptane (250 mL). The filtered solid is dried under vacuum at 45° C. overnight to give the title compound (63.5 g, 79% yield). ES/MS m/z: 196 (M+H).

Preparation 12

1-(6-chloro-1,3-dihydropyrrolo[3,4-c]pyridin-2-yl)ethanone

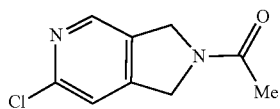 [SMILES: CC(=O)N1Cc2cnc(Cl)cc2C1]

Scheme 4, step A: To a scintillation vial is added 6-chloro-2,3-dihydro-1H-pyrrolo[3,4-c]pyridine;hydrochloride (1.6 g, 8.4 mmol), dichloromethane (21 mL) and N,N-diisopropylethylamine (6 mL, 34 mmol). The mixture is capped, cooled to 0° C. in an ice bath and acetyl chloride (0.7 mL, 10 mmol) is added dropwise. The reaction mixture is removed from ice bath and is stirred at room temperature for 24 h. Saturated aqueous sodium bicarbonate solution (20 mL) and water (5 mL) is added and stirred 5 minutes. The organic layer is removed. The aqueous layer is extracted with dichloromethane (2×10 mL). The combined organic phases are dried over magnesium sulfate, filtered, and concentrated under reduced pressure. The residue is dissolved in dichloromethane, loaded on silica cartridge and purified via flash chromatography eluting with hexanes:acetone [60:40 to 0:100] to give the title compound 1-(6-chloro-1,3-dihydropyrrolo[3,4-c]pyridin-2-yl)ethanone (1.51 g, 7.7 mmol, 91% yield). ES/MS m/z: 197 (M+H).

Preparation 13

Tert-butyl (2 S,4R)-4-[(2-acetyl-1,3-dihydropyrrolo[3,4-c]pyridin-6-yl)oxy]-2-methyl-pyrrolidine-1-carboxylate

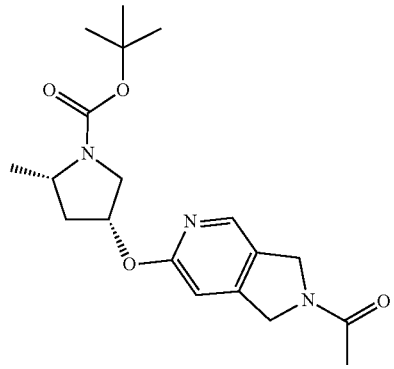 [SMILES: CC(=O)N1Cc2cnc(O[C@@H]3C[C@H](C)N(C(=O)OC(C)(C)C)C3)cc2C1]

Scheme 4, step B: To a scintillation vial is added tert-butyl (2S,4R)-4-hydroxy-2-methyl-pyrrolidine-1-carboxylate (0.3 g, 1.49 mmol), 1-(6-chloro-1,3-dihydropyrrolo[3,4-c]pyridin-2-yl)ethanone (0.35 g, 1.78 mmol) and tetrahydrofuran (6 mL). Mixture is stirred at RT to give a white suspension. Potassium tert-butoxide (0.35 g, 3.09 mmol) is added portion wise. The mixture is capped and is heated at 45° C. for 5 hours. The mixture poured into a separatory funnel containing water (30 mL) and ethyl acetate (30 mL). The organic layer is separated and aqueous phase extracted with ethyl acetate (2×30 mL). The combined organic phase is dried over magnesium sulfate, filtered, and concentrated under reduced pressure. The residue is purified via flash chromatography to give the title compound tert-butyl (2 S,4R)-4-[(2-acetyl-1,3-dihydropyrrolo[3,4-e]pyridin-6-yl)oxy]-2-methyl-pyrrolidine-1-carboxylate (0.121 g, 0.334 mmol, 22% yield). ES/MS m/z: 306 (M+H—C₄H₉).

Preparation 14

1-[6-[(3R,5S)-5-methylpyrrolidin-3-yl]oxy-1,3-dihydropyrrolo[3,4-c]pyridin-2-yl]ethanone;hydrochloride

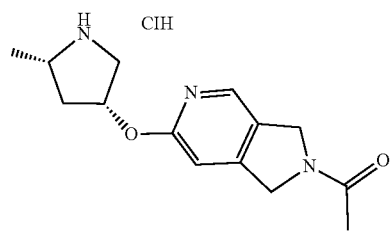

Scheme 4, step C: To a solution of tert-butyl (2S,4R)-4-[(2-acetyl-1,3-dihydropyrrolo[3,4-c]pyridin-6-yl)oxy]-2-methyl-pyrrolidine-1-carboxylate (0.120 g, 0.332 mmol) in dichloromethane (3 mL) is added hydrochloric acid in 1,4-dioxane (0.4 mL, 2 mmol, 4 M solution). The mixture is stirred at room temperature for 3 h. The suspension is concentrated under reduced pressure and the residue is placed under vacuum for 1 h to give 1-[6-[(3R,5S)-5- methylpyrrolidin-3-yl]oxy-1,3-dihydropyrrolo[3,4-c]pyridin-2-yl]ethanone;hydrochloride (0.099 g, 0.299 mmol, 100% yield). MS m/z: 262 (M+H).

Preparation 15

1-(3-bromo-5,7-dihydropyrrolo[3,4-b]pyridin-6-yl)ethanone

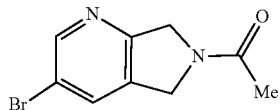 [SMILES: CC(=O)N1Cc2cc(Br)cnc2C1]

Scheme 5, step A: To a 0° C. solution of 3-bromo-6,7-dihydro-5H-pyrrolo[3,4-b]pyridine;hydrochloride (0.52 g, 2.2 mmol) in dichloromethane (6 mL) is dropwise added N,N-diisopropylethylamine (1.5 mL, 8.6 mmol) and acetyl chloride (0.2 mL, 3 mmol). The reaction mixture is stirred at room temperature for 24 h. Added saturated aqueous sodium bicarbonate solution (15 mL) and stirred 5 min and removed the organic layer. The aqueous layer is extracted with dichloromethane (2×25 mL). The combined organic phase is dried over magnesium sulfate, filtered, and concentrated under reduced pressure. The residue is dissolved in dichloromethane, adsorbed onto celite, and purified via flash chromatography (silica gel) eluting with hexanes:acetone [50:50 to 0:100] to give 1-(3-bromo-5,7-dihydropyrrolo[3,4-b]pyridin-6-yl)ethanone (0.440 g, 1.8 mmol, 83% yield). ES/MS m/z: 241 and 243 (M and M+2).

Preparation 16 tert-butyl (2S,4R)-4-[(6-acetyl-5,7-dihydropyrrolo[3,4-b]pyridin-3-yl)oxy]-2-methyl-pyrrolidine-1-carboxylate

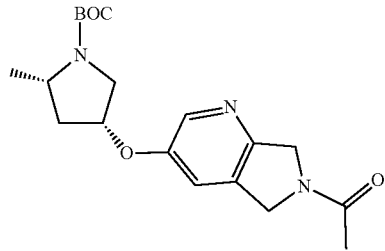 [SMILES: CC(=O)N1Cc2cc(O[C@@H]3C[C@H](C)N(C(=O)OC(C)(C)C)C3)cnc2C1]

Scheme 5, step B: To a scintillation vial with tert-butyl (2S,4R)-4-hydroxy-2-methyl-pyrrolidine-1-carboxylate (0.399 g, 1.98 mmol), 1-(3-bromo-5,7-dihydropyrrolo[3,4-b]pyridin-6-yl)ethanone (0.300 g, 1.24 mmol), cesium carbonate (1.22 g, 3.74 mmol) and methanesulfonato(2-di-t-butylphosphino-3,4,5,6-tetramethyl-2',4',6'-tri-i-propylbiphenyl)(2'-amino-1,1'-biphenyl-2-yl)palladium(II) (0.28 g, 0.33 mmol) is added toluene (12 mL) and the mixture is capped and is heated at 75° C. for 72 hours. The reaction mixture is cooled and filtered through celite using acetone to rinse. The filtrate is concentrated under reduced pressure. The residue is taken up in dichloromethane and purified via flash chromatography (silica gel) eluting with hexane:acetone [1:1 to 0:1] to give tert-butyl (2S,4R)-4-[(6-acetyl-5,7-dihydropyrrolo[3,4-b]pyridin-3-yl)oxy]-2-methyl-pyrrolidine-1-carboxylate (0.109 g, 0.301 mmol, 24% yield). ES/MS m/z: 306 (M+H—$C_4H_9$).

Preparation 17

1-[3-[(3R,5S)-5-methylpyrrolidin-3-yl]oxy-5,7-dihydropyrrolo[3,4-b]pyridin-6-yl]ethanone;hydrochloride

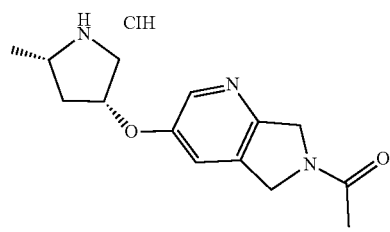

Scheme 5, step C: To a solution of tert-butyl (2S,4R)-4-[(6-acetyl-5,7-dihydropyrrolo[3,4-b]pyridin-3-yl)oxy]-2-methyl-pyrrolidine-1-carboxylate (0.108 g, 0.299 mmol) in dichloromethane (3 mL) is added hydrochloric acid in 1,4-dioxane (0.4 mL, 2 mmol, 4 M solution). The mixture is stirred at room temperature for 2.5 h. The suspension is concentrated under reduced pressure and the residue is placed under vacuum for 1 h to give 1-[3-[(3R,5S)-5-methylpyrrolidin-3-yl]oxy-5,7-dihydropyrrolo[3,4-b]pyridin-6-yl]ethanone;hydrochloride (0.089 g, 0.299 mmol, 100% yield). MS m/z: 262 (M+H).

Preparation 18

1-(6-fluoro-2-methyl-1,3-benzothiazol-5-yl)ethanone

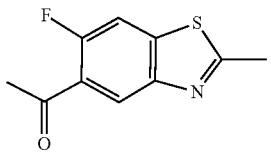

Scheme 3, step A: Purge a flask containing 5-bromo-6-fluoro-2-methyl-1,3-benzothiazole (30.6 g, 124 mmol) and [1,3-bis(diphenylphosphino)propane]palladium (II) dichloride (2.32 g, 3.85 mmole) with nitrogen and add ethylene glycol (240 mL) and trimethylamine (50 mL, 359 mmol) and 1-vinyloxybutane (80 mL, 618 mmol). Heat the reaction at 100° C. for 18 h. Cool the reaction to room temperature and add 2.5 M aqueous HCl (500 mL, 1.300 mol) and stir for 1 hour. And ethyl acetate (400 mL) and remove the organic layer. Extract the aqueous layer with EtOAc (2×225 mL). Dry the combined organic layer over magnesium sulfate, filter, and concentrate. Suspend the crude product in 65:35 water:MeOH, filter the slurry, and dry the solid to afford the title compound 1-(6-fluoro-2-methyl-1,3-benzothiazol-5-yl)ethanone (16.7 g, 79.8 mmol, 64% yield). ES/MS m/z: 210 (M+H).

Alternative Preparation of 1-(6-fluoro-2-methyl-1,3-benzothiazol-5-yl)ethanone

To a flask is added 5-bromo-6-fluoro-2-methyl-1,3-benzothiazole (72.0 g, 293 mmol), 1,3-bis(diphenylphosphino)

propane (2.41 g, 5.85 mmol) and palladium(II) acetate (0.657 g, 2.93 mmol) at room temperature under $N_2$. To the flask is added ethylene glycol (720 mL), 1-vinyloxybutane (189 mL, 1460 mmol) and triethylamine (124 mL, 878 mmol). $N_2$ is bubbled through the reaction mixture for 30 minutes with stirring at room temperature, then the reaction mixture is stirred overnight in a 115° C. heating block with a condenser fitted (internal temperature 98° C.). The reaction mixture is cooled to room temperature and is poured into a mixture of aq. 2M HCl (576 mL) and ice (50 g) over 15 minutes with ice-water bath cooling, maintaining an internal temperature below 20° C. during the addition. The mixture is stirred at room temperature for 5 minutes, then is stirred in a 41° C. heating block for 30 minutes (internal temperature 40° C.). The reaction mixture is diluted with EtOAc (500 mL) and the mixture is stirred at room temperature for 10 minutes, then is filtered through diatomaceous earth. The filtrate is transferred to a separating funnel and the layers are separated. The aqueous layer is extracted with EtOAc (500 mL), then the combined organics are washed with sat. aq. NaCl solution (500 mL), dried over $Na_2SO_4$ and concentrated. The resultant residue is suspended in 35% MeOH/water (162 mL) and the mixture is vigorously agitated in a 45° C. water bath on a rotary evaporator for 30 minutes, then is cooled to room temperature and filtered. The filtered solid is dried under vacuum at 40° C. overnight to give the title compound (57.48 g, 93% yield) as a brown solid. ES/MS m/z: 210 (M+H)

mmol) and NADP (0.501 g) at room temperature. The mixture is stirred in a 37° C. heating block (internal temperature 36° C.) open to air overnight, then to the mixture is added KRED-P3-C12 (2.51 g), magnesium sulfate (0.0865 g, 0.718 mmol) and NADP (0.251 g) and the reaction mixture is stirred in a 37° C. heating block (internal temperature 36° C.) overnight open to air under a stream of $N_2$ gas. To the reaction mixture is added 2-propanol (146 mL), KRED-P3-C12 (2.51 g), magnesium sulfate (0.0865 g, 0.718 mmol) and NADP (0.251 g) and the reaction mixture is stirred in a 37° C. heating block (internal temperature 36° C.) overnight open to air under a stream of $N_2$ gas. To the reaction mixture is added 2-propanol (91.5 mL), KRED-P3-C12 (0.501 g), magnesium sulfate (0.0288 g, 0.239 mmol) and NADP (0.0501 g) and the reaction mixture is stirred in a 37° C. heating block (internal temperature 36° C.) overnight open to air under a stream of $N_2$ gas. The reaction mixture is diluted with water (400 mL) and EtOAc (400 mL) and filtered through diatomaceous earth, washing with water (100 mL) and EtOAc (100 mL). The filtrate is transferred to a separating funnel and the layers are separated. The aqueous layer is extracted with EtOAc (500 mL), then the combined organics are washed with water (1 L), dried over $Na_2SO_4$ and concentrated to give the title compound (48.7 g, 96% yield) as a brown solid. Optical rotation $[\alpha]D^{20}=-35°$ (c=0.2, MeOH). ES/MS m/z: 212 (M+H).

Preparation 19

(1S)-1-(6-fluoro-2-methyl-1,3-benzothiazol-5-yl)ethanol

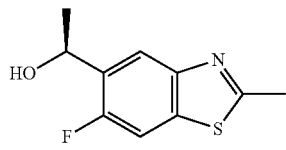

Scheme 3, step B: To an autoclave is added 1-(6-fluoro-2-methyl-1,3-benzothiazol-5-yl)ethanone (16.7 g, 79.8 mmol) and (R)-Rucy-xylBinap (CAS #1384974-38-2) (0.465 g, 0.385 mmol) and a 1M solution of potassium tert-butoxide in tert-butanol (3.5 mL, 3.5 mmol) and toluene (240 mL). The autoclave is cooled to −10° C. and charged to 450 psi with hydrogen with stirring at 500 rpm for 4.5 hours. The reaction is warmed to room temperature and stirred for 15 hours. The reaction mixture is concentrated. The residue is purified via flash chromatography (silica gel) eluting with a gradient of 0-40% EtOAc in hexanes to give (1S)-1-(6-fluoro-2-methyl-1,3-benzothiazol-5-yl)ethanol (15.8 g, 74.8 mmol, 94% yield). ES/MS m/z: 212 (M+H). $[\alpha]_D^{20}=-38.6°$ (c=0.2, MeOH).

Alternative Preparation of (1S)-1-(6-fluoro-2-methyl-1,3-benzothiazol-5-yl)ethanol To a flask is added 1-(6-fluoro-2-methyl-1,3-benzothiazol-5-yl)ethanone (50.1 g, 239 mmol), 2-propanol (311 mL), aq. pH 7 potassium phosphate buffer solution (0.1 M, 752 mL), KRED-P3-C12 (5.51 g; Codexis Ketoreductase (KRED), lyophyilized enzyme powder, carbonyl reductase, CAS #77106-95-7), magnesium sulfate (0.173 g, 1.44

Preparation 20

5-[(1R)-1-chloroethyl]-6-fluoro-2-methyl-1,3-benzothiazole

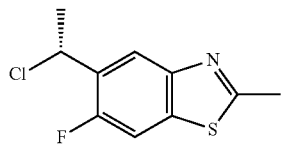

Scheme 3, step C: To a solution of (S)-1-(6-fluoro-2-methylbenzo[d]thiazol-5-yl)ethan-1-ol (15.8 g, 74.8 mmol) in dioxane (400 mL) is added 1-formylpyrrolidine (3.7 mL, 38 mmol) and benzoyl chloride (22 mL, 187 mmol). The reaction is stirred at room temperature for 36 h. The reaction is cooled to 0° C. and ethyl acetate (250 mL) is added followed by dropwise addition of N,N-dimethylethylenediamine (12 mL, 110 mmol). The solution is warmed to room temperature and stirred for 10 minutes. To the solution is added saturated aqueous citric acid solution (200 mL). The solution is diluted with ethyl acetate (250 mL) and water (250 mL). The aqueous layer is removed and extracted with ethyl acetate (2×125 mL). The combine organic layers are washed with saturated aqueous sodium carbonate (200 mL). This aqueous wash is back extracted with ethyl acetate (100 mL). The combined organic layers are washed with brine (100 mL) and then dried over magnesium sulfate, filtered, and concentrated. The residue is purified by via flash chromatography (silica gel) eluting with hexanes:DCM (97:3 to 50:50) to give 5-[(1R)-1-chloroethyl]-6-fluoro-2-methyl-1,3-benzothiazole (13.2 g, 57.6 mmol, 77% yield). ES/MS m/z: 230 (M+H).

Example 1

1-(2-(((3R,5S)-1-((6-fluoro-2-methylbenzo[d]thi-azol-5-yl)methyl)-5-methylpyrrolidin-3-yl)oxy)-5,7-dihydro-6H-pyrrolo[3,4-d]pyrimidin-6-yl)ethan-1-one

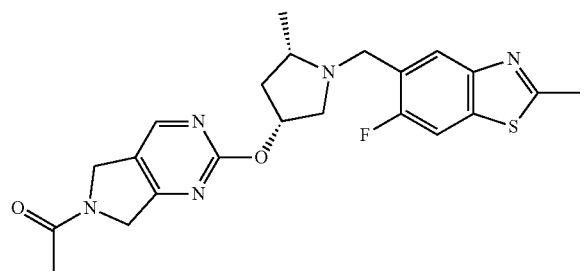 [SMILES: CC(=O)N1Cc2cnc(O[C@@H]3C[C@H](C)N(Cc4cc5nc(C)sc5cc4F)C3)nc2C1]

Scheme 1, step D (X=N): To a solution of 6-fluoro-2-methyl-1,3-benzothiazole-5-carbaldehyde (0.920 g, 4.71 mmol) and 1-(2-(((3R,5S)-5-methylpyrrolidin-3-yl)oxy)-5,7-dihydro-6H-pyrrolo[3,4-d]pyrimidin-6-yl)ethan-1-one hydrochloride (1.48 g, 4.95 mmol) in DCM (46 mL) is added DIPEA (2.4 mL, 14 mmol). The resulting solution is stirred at RT for 1 h. To the solution is added NaBH(OAc)$_3$ (3.0 g, 14.2 mmol). The resulting solution is stirred at RT for 16 h. The reaction mixture is quenched slowly with saturated aqueous NaHCO$_3$ (10 mL) and diluted with water (50 mL). The aqueous layer is extracted with DCM (2×50 mL). The combined organic extracts are dried over MgSO$_4$, filtered, and concentrated under reduced pressure. The resulting residue is dissolved in DCM and purified via flash chromatography over silica gel, eluting with a gradient of 10-100% acetone in hexanes followed by isocratic 10% methanol in EtOAc to obtain the title compound after solvent evaporation of the desired chromatographic fractions (1.68 g, 81% yield). ES/MS m/z: 442 (M+H); [α]$_D^{20}$=+55.3° (c=0.2, MeOH).

Alternative Procedure for Example 1

To a flask is added 1-(2-(((3R,5S)-5-methylpyrrolidin-3-yl)oxy)-5,7-dihydro-6H-pyrrolo[3,4-d]pyrimidin-6-yl)ethan-1-one (18.2 g, 45.1 mmol) and DCM (178 mL). The mixture is stirred in an ice-water bath (internal temperature 5° C.) and to the mixture is added 6-fluoro-2-methyl-1,3-benzothiazole-5-carbaldehyde (8.9 g, 45.1 mmol), pyridine (7.3 mL, 90 mmol) and NaBH(OAc)$_3$ (19.1 g, 90.1 mmol). The reaction mixture is stirred at RT overnight (internal temperature 20° C.), cooled in an ice-water bath, and aqueous 10% Na$_2$CO$_3$ solution (130 mL) is added over 5 min, maintaining an internal temperature below 15° C. during the addition. The mixture is stirred vigorously at RT for 15 min, the layers are separated, and the aqueous layer is extracted with DCM (2×90 mL). The combined organic extracts are dried over Na$_2$SO$_4$, filtered, and the filtrate is concentrated to give a residue, which is purified by flash chromatography over silica, using a gradient of 0-15% isopropanol/DCM. The product-containing fractions are concentrated under reduced pressure. The resulting residue is concentrated from heptane (100 mL) to obtain the title compound (15.64 g, 76% yield) as a cream-colored solid. The solid is combined with two other lots of similar purity and the combined material (19.86 g, 43.65 mmol) is combined with EtOAc (149 mL) and heptane (149 mL) at RT. The mixture is stirred vigorously in a 45° C. heating block for 30 min, cooled to RT and stirred for 15 min, and is filtered. The filtered solid is dried under vacuum at 40° C. overnight to give the title compound (18.81 g, 96% yield) as an off-white solid. ES/MS m/z: 442 (M+H); [α]D$^{20}$=+59.8° (c=0.2, MeOH).

Example 2

1-(2-(((3R,5S)-1-((6-fluoro-2-methylbenzo[d]thi-azol-5-yl)methyl)-5-methylpyrrolidin-3-yl)oxy)-5,7-dihydro-6H-pyrrolo[3,4-b]pyridin-6-yl)ethan-1-one

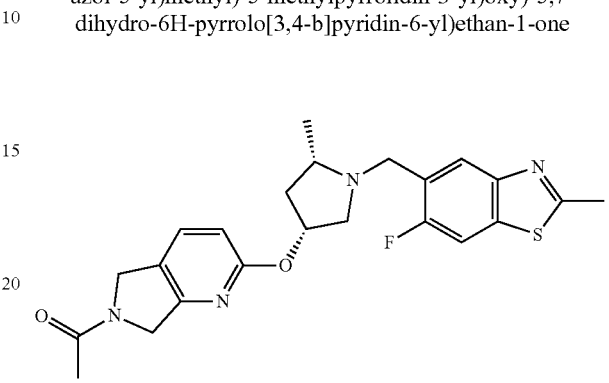

Scheme 1, step D (X=CH): To a solution of 6-fluoro-2-methyl-1,3-benzothiazole-5-carbaldehyde (0.19 g, 0.95 mmol) and 1-(2-(((3R,5S)-5-methylpyrrolidin-3-yl)oxy)-5,7-dihydro-6H-pyrrolo[3,4-b]pyridin-6-yl)ethan-1-one hydrochloride (0.28 g, 0.94 mmol) in DCM (9 mL) is added DIPEA (0.45 mL, 2.6 mmol). The resulting solution is stirred at RT for 40 min. To the solution is added NaBH(OAc)$_3$ (0.65 g, 3.04 mmol). The resulting solution is stirred at RT for 17 h. The reaction mixture is quenched slowly with saturated aqueous NaHCO$_3$ (5 mL). The aqueous layer is extracted with DCM (2×5 mL). The combined organic extracts are dried over MgSO$_4$, filtered, and concentrated under reduced pressure. The resulting residue is dissolved in DCM and purified via flash chromatography over silica gel, eluting with a gradient of 40-100% acetone in hexanes, to obtain the title compound after solvent evaporation of the desired chromatographic fractions (0.27 g, 65% yield). ES/MS m/z: 441 (M+H); [α]D$^{20}$=+101.4° (c=0.2, MeOH).

Alternative Preparation of 1-(2-(((3R,5S)-1-((6-fluoro-2-methylbenzo[d]thiazol-5-yl)methyl)-5-methylpyrrolidin-3-yl)oxy)-5,7-dihydro-6H-pyrrolo[3,4-b]pyridin-6-yl)ethan-1-one Preparation of 4-Methylbenzenesulfonic acid;(3R,5S)-5-methylpyrrolidin-3-ol

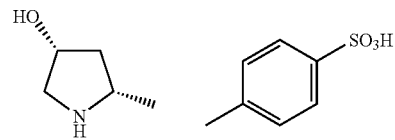

To a flask is added tert-butyl (2S,4R)-4-hydroxy-2-methyl-pyrrolidine-1-carboxylate (53.0 g, 263 mmol) and 2-propanol (265 mL) at room temperature. The mixture is stirred at room temperature (internal temperature 20° C.) and p-toluenesulfonic acid monohydrate (60.1 g, 316 mmol) is added in one portion. The reaction mixture is stirred in a 62° C. heating block overnight, then is cooled to room temperature and concentrated to approximately 150 mL total volume. The mixture is diluted with MTBE (530 mL) and the mixture is stirred vigorously at room temperature for 30 minutes and then is filtered under flow of N₂ gas. The filtered solid is dried under vacuum at 40° C. for 2 hours to provide 4-methylbenzenesulfonic acid;(3R,5S)-5-methylpyrrolidin-3-ol (67.6 g, 93% yield) as a white solid. ES/MS m/z: 102 (M+H).

Preparation of (3R,5S)-1-[(6-Fluoro-2-methyl-1,3-benzothiazol-5-yl)methyl]-5-methyl-pyrrolidin-3-ol

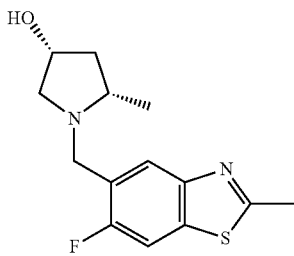 [SMILES: Cc1nc2cc(CN3C[C@H](O)C[C@@H]3C)c(F)cc2s1]

To a flask is added 4-methylbenzenesulfonic acid;(3R,5S)-5-methylpyrrolidin-3-ol (61.9 g, 226 mmol), EtOAc (850 mL) and 6-fluoro-2-methyl-1,3-benzothiazole-5-carbaldehyde (42.5 g, 216 mmol) at room temperature. The reaction mixture is stirred in an ice-water bath (internal temperature 3° C.) and triethylamine (60.1 mL, 431 mmol) is added in one portion. The reaction mixture is stirred in an ice-water bath for 30 minutes, then sodium triacetoxyborohydride (91.4 g, 431 mmol) is added in one portion. The reaction mixture is stirred in an ice-water bath for 10 minutes, then at room temperature for 2 hours (internal temperature 20° C.). The reaction mixture is stirred in an ice-water bath and 15% aq. KHSO₄ solution (650 mL) is added over 5 minutes, maintaining an internal temperature below 15° C. during the addition. The mixture is stirred vigorously at room temperature for 1 hour, then sat. aq. citric acid solution (100 mL) is added and the mixture is stirred at room temperature for 5 minutes, then the layers are separated. The aqueous layer is washed with EtOAc (400 mL), then the aqueous layer is stirred in an ice-water bath and solid Na₂CO₃ (80 g) is added portionwise over 10 minutes with vigorous stirring until pH=10 (measured by pH paper). The aqueous layer is then extracted with EtOAc (3×400 mL). The combined organics are dried over Na₂SO₄ and concentrated to give a residue that is crushed into a fine powder using a pestle and mortar, then is combined with 25% MTBE/heptane (280 mL). The mixture is stirred vigorously in a 45° C. heating block for 1 hour, then at room temperature for 1 hour and then is filtered to give the first batch of filtered solid. The filtrate is concentrated, then the residue is combined with 25% MTBE/heptane (40 mL) and the mixture is stirred vigorously at room temperature for 30 minutes and then is filtered to give the second batch of filtered solid. The first and second batches of filtered solids are combined and the mixture is ground up with a spatula, then is dried under vacuum at room temperature overnight to provide (3R,5S)-1-[(6-fluoro-2-methyl-1,3-benzothiazol-5-yl)methyl]-5-methyl-pyrrolidin-3-ol (53.3 g, 87% yield) as a cream-coloured solid. ES/MS m/z: 281 (M+H).

Preparation of final title compound 1-(2-(((3R,5S)-1-((6-fluoro-2-methylbenzo[d]thiazol-5-yl)methyl)-5-methylpyrrolidin-3-yl)oxy)-5,7-dihydro-6H-pyrrolo[3,4-b]pyridin-6-yl)ethan-1-one To a flask is added (3R,5S)-1-[(6-fluoro-2-methyl-1,3-benzothiazol-5-yl)methyl]-5-methyl-pyrrolidin-3-ol (26.9 g, 95.0 mmol), 1-(2-chloro-5,7-dihydropyrrolo[3,4-b]pyridin-6-yl)ethanone (22.1 g, 109 mmol), cesium carbonate (92.8 g, 285 mmol), MorDalPhos (1.76 g, 3.80 mmol), palladium (II)(pi-cinnamyl) chloride dimer (984 mg, 1.90 mmol) and toluene (538 mL) at room temperature. N₂ gas is bubbled through the mixture at room temperature with stirring for 30 minutes, then the reaction mixture is stirred in a 86° C. heating block overnight (internal temperature 80° C.). The reaction mixture is cooled to room temperature and diluted with EtOAc (269 mL) and diatomaceous earth (27 g) is added. The mixture is stirred at room temperature for 5 minutes, then is filtered through diatomaceous earth, washing with EtOAc (200 mL). The filtrate is concentrated to give a residue, which is dissolved in EtOAc (100 mL) and the mixture is passed through a short pad of silica gel (300 g), eluting with EtOAc (2 L) and then with 20% IPA/EtOAc (2 L). The IPA/EtOAc fraction is concentrated to give a residue, which is dried under vacuum at room temperature for 1 hour to give the title compound (42.1 g, 88% yield, 88% purity by mass) as a pale brown foam.

The foam is combined with another lot of similar purity and the combined material (46.0 g, 92.3 mmol) is combined with MTBE (230 mL) and heptane (230 mL) at room temperature. The mixture is stirred vigorously in a 45° C. heating block for 1 hour, then at room temperature for 30 minutes and then is filtered. The filtered solid is combined with EtOAc (400 mL) and SiliaMetS Thiol (40 g) is added. The mixture is agitated on a rotary evaporator at room temperature for 1 hour, then is filtered. The filtrate is concentrated to give a residue, which is combined with 25% EtOAc/heptane (400 mL) and the mixture is stirred vigorously in a 50° C. heating block for 1 hour, then at room temperature for 10 minutes, then is filtered, keeping aside the first batch of filtrate. The filtered solid is combined with 35% EtOAc/heptane (400 mL) and the mixture is stirred vigorously in a 50° C. heating block for 1 hour, then at room temperature for 10 minutes, then is filtered, keeping aside the second batch of filtrate. The filtered solid is combined with EtOAc (500 mL) and 15% aq. KHSO₄ solution (500 mL). The mixture is stirred vigorously at room temperature for 15 minutes, then is transferred to a separating funnel and the layers are separated, leaving a rag layer in the organics. The organic layer is further extracted with 15% aq. KHSO₄ solution (100 mL), leaving a rag layer in the organics. The rag layer is removed from the organics and is diluted with CH₂Cl₂ (100 mL) and 15% aq. KHSO₄ solution (100 mL) and the layers are separated. The combined aqueous layers are stirred in an ice-water bath and solid Na₂CO₃ (100 g) is added portionwise over 5 minutes with stirring (pH measured as 10 by pH paper). The mixture is extracted with CH₂Cl₂ (2×500 mL) and the combined organics are dried over Na₂SO₄ and concentrated to give the first batch of crude product. The first and second batches of filtrates from the filtrations are combined and concentrated, then the residue is combined with EtOAc (100 mL) and 15% aq. KHSO₄ solution (100 mL). The mixture is stirred vigorously at room temperature for 15 minutes, then is transferred to a separating funnel and the layers are separated. The aqueous layer is stirred in an ice-water bath and solid Na₂CO₃ (15 g) is added portionwise over 5 minutes with stirring (pH measured as 10 by pH paper). The mixture is extracted with CH$_2$Cl$_2$ (2×100 mL) and the combined organics are dried over Na$_2$SO$_4$ and concentrated to give a residue which is combined with 25% EtOAc/heptane (80 mL) and the mixture is stirred vigorously in a 50° C. heating block for 30 minutes, then at room temperature for 10 minutes, then is filtered to give the second batch of crude product. The two batches of crude product are combined with 25% EtOAc/heptane (400 mL) and the mixture is stirred vigorously in a 50° C. heating block for 30 minutes, then at room temperature for 10 minutes, then is filtered. The filtered solid is dried under vacuum at room temperature 3 days to provide the final title compound (37.4 g, 90% yield) as a white solid. ES/MS m/z: 441 (M+H). Optical rotation $[\alpha]D_{20}$=+104.0° (c=0.2, MeOH).

Example 3

1-[6-[(3R,5S)-1-[(6-fluoro-2-methyl-1,3-benzothiazol-5-yl)methyl]-5-methyl-pyrrolidin-3-yl]oxy-1,3-dihydropyrrolo[3,4-c]pyridin-2-yl]ethanone

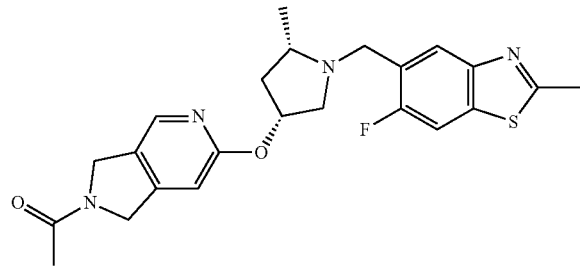 [SMILES: CC(=O)N1Cc2cnc(O[C@@H]3C[C@H](C)N(Cc4cc5nc(C)sc5cc4F)C3)cc2C1]

Scheme 4, step D: To a scintillation vial containing 6-fluoro-2-methyl-1,3-benzothiazole-5-carbaldehyde (0.071 g, 0.363 mmol) and 1-[6-[(3R,5S)-5-methylpyrrolidin-3-yl]oxy-1,3-dihydropyrrolo[3,4-c]pyridin-2-yl]ethanone;hydrochloride (0.1 g, 0.335 mmol) in dichloromethane (3.5 mL) is added N,N-diisopropylethylamine (0.175 mL, 1 mmol). The solution is stirred at room temperature and sodium triacetoxyborohydride (0.220 g, 1.038 mmol) is added. The solution is stirred at room temperature for 20 hours. The reaction is slowly quenched with saturated aqueous sodium bicarbonate (3 mL). The aqueous layer is extracted with dichloromethane (3×5 mL). The combined organic phase is dried over magnesium sulfate, filtered, and concentrated under reduced pressure. The residue is purified by reverse phase HPLC (solvent A: aqueous 10 mM ammonium bicarbonate pH=10/5% MeOH, solvent B: acetonitrile, Phenomenex Kinetex EVO C18, 100×30 mm column, 50° C. column heater) to give 1-[6-[(3R,5S)-1-[(6-fluoro-2-methyl-1,3-benzothiazol-5-yl)methyl]-5-methyl-pyrrolidin-3-yl]oxy-1,3-dihydropyrrolo[3,4-c]pyridin-2-yl]ethanone (0.089 g, 0.203 mmol, 56% yield). ES/MS m/z: 441 (M+H). $[\alpha]D^{20}$=+22.5° (c=0.2, MeOH).

Example 4

1-[3-[(3R,5S)-1-[(6-fluoro-2-methyl-1,3-benzothiazol-5-yl)methyl]-5-methyl-pyrrolidin-3-yl]oxy-5,7-dihydropyrrolo[3,4-b]pyridin-6-yl]ethanone

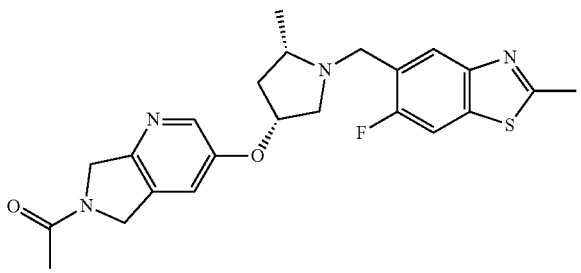 [SMILES: CC(=O)N1Cc2cc(O[C@@H]3C[C@H](C)N(Cc4cc5nc(C)sc5cc4F)C3)cnc2C1]

Scheme 5, step D: To a solution of 6-fluoro-2-methyl-1,3-benzothiazole-5-carbaldehyde (0.057 g, 0.292 mmol) and 1-[3-[(3R,5S)-5-methylpyrrolidin-3-yl]oxy-5,7-dihydropyrrolo[3,4-b]pyridin-6-yl]ethanone;hydrochloride (0.089 g, 0.299 mmol) in dichlormethane (3 mL) is added N,N-diisopropylethylamine (0.15 mL, 0.86 mmol). The solution is stirred at room temperature and sodium triacetoxyborohydride (0.188 g, 0.877 mmol) is added. The solution is stirred at room temperature for 23 hours. The reaction is slowly quenched with saturated aqueous sodium bicarbonate (5 mL). The aqueous layer is extracted with dichloromethane (3×5 mL). The combined organic phase is dried over magnesium sulfate, filtered, and concentrated under reduced pressure. The residue is purified by reverse phase HPLC (solvent A: aqueous 10 mM ammonium bicarbonate pH=10/5% MeOH, solvent B: acetonitrile, Phenomenex Kinetex EVO C18, 100×30 mm column, 50° C. column heater) to give 1-[3-[(3R,5S)-1-[(6-fluoro-2-methyl-1,3-benzothiazol-5-yl)methyl]-5-methyl-pyrrolidin-3-yl]oxy-5,7-dihydropyrrolo[3,4-b]pyridin-6-yl]ethanone (0.055 g, 0.125 mmol, 43% yield). MS m/z: 441 (M+H). $[\alpha]D^{20}$=+50.7° (c=0.2, MeOH).

Example 5

1-[2-[(3R,5S)-1-[(1S)-1-(6-fluoro-2-methyl-1,3-benzothiazol-5-yl)ethyl]-5-methyl-pyrrolidin-3-yl]oxy-5,7-dihydropyrrolo[3,4-d]pyrimidin-6-yl]ethanone

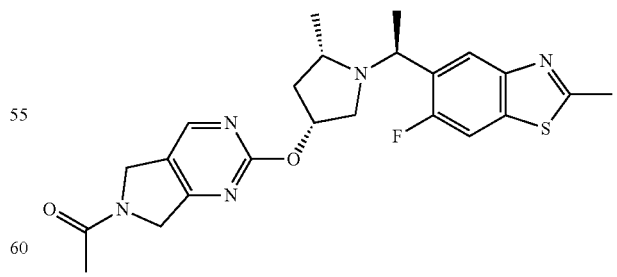

Scheme 3, step D: To a solution of 1-(2-(((3R,5S)-5-methylpyrrolidin-3-yl)oxy)-5,7-dihydro-6H-pyrrolo[3,4-d]pyrimidin-6-yl)ethan-1-one hydrochloride (0.165 g, 0.552 mmol) in acetonitrile (4.0 mL) is added 5-[(1R)-1-chloroethyl]-6-fluoro-2-methyl-1,3-benzothiazole (0.097 g, 0.422 mmol) and cesium carbonate (1.4 g, 4.3 mmol). The suspension is stirred at 68° C. for 21 h. The crude reaction is cooled to room temperature and filtered through celite. The filtrate is concentrated and purified via reverse phase chromatography on a Phenomenex Kinetex EVO C18 column with aqueous 0.1% formic acid:MeCN as the mobile phase. This material is further purified on a Chiralcel OD-H column with 40% MeOH(0.2% IPAm)/CO$_2$ as the mobile phase to give 1-(2-(((3R,5S)-1-((S)-1-(6-fluoro-2-methylbenzo[d]thiazol-5-yl)ethyl)-5-methylpyrrolidin-3-yl)oxy)-5,7-dihydro-6H-pyrrolo[3,4-d]pyrimidin-6-yl)ethan-1-one (0.050 g, 0.110 mmol, 26% yield). MS m/z: 456 (M+H). $[\alpha]_D^{20}=-13.8°$ (c=0.2, MeOH).

Example 6

1-[2-[(3R,5S)-1-[(1S)-1-(6-fluoro-2-methyl-1,3-benzothiazol-5-yl)ethyl]-5-methyl-pyrrolidin-3-yl]oxy-5,7-dihydropyrrolo[3,4-b]pyridin-6-yl]ethanone

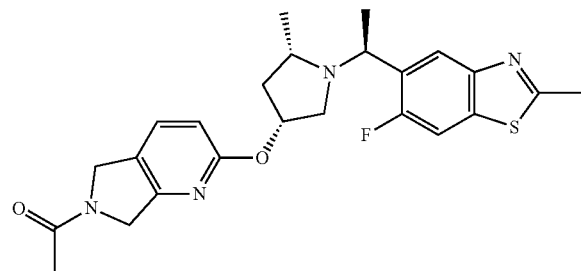 [SMILES: CC(=O)N1Cc2ccc(O[C@@H]3C[C@H](C)N([C@@H](C)c4cc5nc(C)sc5cc4F)C3)nc2C1]

Scheme 3, step D: To a solution of 1-(2-(((3R,5S)-5-methylpyrrolidin-3-yl)oxy)-5,7-dihydro-6H-pyrrolo[3,4-b]pyridin-6-yl)ethan-1-one hydrochloride (0.192 g, 0.644 mmol) in acetonitrile (5.0 mL) is added 5-[(1R)-1-chloroethyl]-6-fluoro-2-methyl-1,3-benzothiazole (0.104 g, 0.452 mmol) and cesium carbonate (1.56 g, 4.79 mmol). The suspension is stirred at 65° C. for 17 h. The crude reaction is cooled to room temperature and filtered through celite. The filtrate is concentrated and purified via flash chromatography (silica gel) eluting with hexanes:(3:1 acetone:DCM) [60:40 to 0:100]. This material is further purified on a Chiralpak AD-H column with 40% MeOH(0.2% IPAm)/CO$_2$ as the mobile phase to give 1-(2-(((3R,5S)-1-((S)-1-(6-fluoro-2-methylbenzo[d]thiazol-5-yl)ethyl)-5-methylpyrrolidin-3-yl)oxy)-5,7-dihydro-6H-pyrrolo[3,4-b]pyridin-6-yl)ethan-1-one (0.033 g, 0.073 mmol, 16% yield). MS m/z: 455 (M+H). $[\alpha]D^{20}=+19.5°$ (c=0.2, MeOH).

In Vitro Human OGA Enzyme Assay

Generation of OGA enzyme

The nucleotide sequence encoding full-length human O-GlcNAc-β-N-acetylglucosaminidase (NM_012215) is inserted into pFastBacl (Invitrogen) vector with an N-terminal poly-histidine (HIS) tag. Baculovirus generation is carried out according to the Bac-to-Bac Baculovirus Expression system (Invitrogen) protocol. Sf9 cells are infected at 1.5×10$^6$ cells/mL using 10 mL of P1 virus per Liter of culture and incubated at 28° C. for 48 hrs. Cells are spun down, rinsed with PBS and the pellets stored at −80° C. The above OGA protein (His-OGA) is purified as follows: 4 L of cells are lysed in 200 mL of buffer containing 50 mM Tris, pH 8.0, 300 mM NaCl, 10% glycerol, 10 mM imidazole, 1 mM dithiothreitol (DTT), 0.1% Triton™ X-100, 4 tablets of protease inhibitors (complete EDTA-Free, Roche) for 45 min at 4° C. This cell lysate is then spun for 40 min at 16500 rpm at 4° C., and supernatant incubated with 6 mL of Ni-NTA resin (nickel-nitrilotriacetic acid) for 2 h at 4° C.

Resin is then packed onto column and washed with 50 mM Tris, pH 8.0, 300 mM NaCl, 10% glycerol, 10 mM imidazole, 0.1% Triton™ X-100, 1 mM DTT, followed by 50 mM Tris, pH 8.0, 150 mM NaCl, 10 mM imidazole, 10% glycerol, 1 mM DTT. The proteins are eluted with 50 mM Tris, pH 8.0, 150 mM NaCl, 300 mM imidazole, 10% glycerol, 1 mM DTT. Pooled His-OGA containing fractions are concentrated to 6 ml and loaded onto Superdex75 (16/60). The protein is eluted with 50 mM Tris, pH 8.0, 150 mM NaCl, 10% glycerol, 2 mM DTT. Fractions containing His-OGA are pooled and protein concentration measured with BCA (Bradford Colorimetric Assay).

OGA Enzyme Assay

The OGA enzyme catalyses the removal of O-GlcNAc from nucleocytoplasmic proteins. To measure this activity Fluorescein di-N-acetyl-β-N-acetyl-D-glucosaminide (FD-GlcNAc, Kim, Eun Ju; Kang, Dae Ook; Love, Dona C.; Hanover, John A. Carbohydrate Research (2006), 341(8), 971-982) is used as a substrate at a final concentration of 6.7 µM. This fluorogenic substrate becomes fluorescent upon cleavage by OGA, so that the enzyme activity can be measured by the increase in fluorescence detected at 535 nm (excitation at 485 nm).

The assay buffer is prepared to give a final concentration of 50 mM H$_2$NaPO$_3$-HNa$_2$PO$_3$, 0.01% bovine serum albumin and 0.01% Triton™ X-100 in water, at pH 7. Compounds to be tested are diluted in pure dimethyl sulfoxide (DMSO) using ten point concentration response curves. Maximal compound concentration in the reaction mixture is 30 or 1 µM. Compounds at the appropriate concentration are pre-incubated with OGA enzyme for 30 minutes before the reaction is started by the addition of substrate. The final enzyme concentration is 3.24 nM or 0.5 nM, for the 30 or 1 µM maximal compound concentration, respectively. Reactions are allowed to proceed for 60 min at room temperature. Then, without stopping the reaction, fluorescence is read. IC$_{50}$ values are calculated by plotting the normalized data vs. log of the compound and fitting the data using a four parameter logistic equation.

The compounds of Examples 1 through 6 were tested essentially as described above.

TABLE 1

| Example | IC$_{50}$ (nM) |
| --- | --- |
| 1 | 0.465 ± 0.224 (n = 5) |
| 2 | 0.214 ± 0.037 (n = 4) |
| 3 | 0.782 ± 0.087 (n = 3) |
| 4 | 0.592 ± 0.068 (n = 2) |
| 5 | 0.495 ± 0.109 (n = 3) |
| 6 | 0.385 ± 0.088 (n = 3) |

The results in Table 1 demonstrate that the compounds of Examples 1 through 6 inhibit OGA enzyme activity in vitro.

We claim:
1. A compound of the formula:

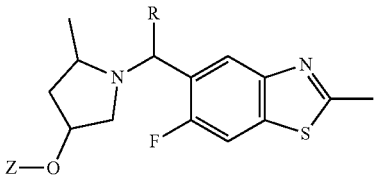

wherein
R is hydrogen or methyl; and
Z is:

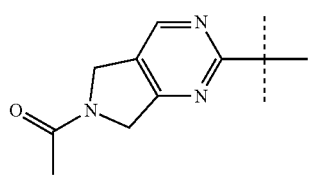

or a pharmaceutically acceptable salt thereof.

2. The compound according to claim 1 wherein the methyl at position 5 on the pyrrolidine ring is in the cis configuration relative to the oxygen at position 3:

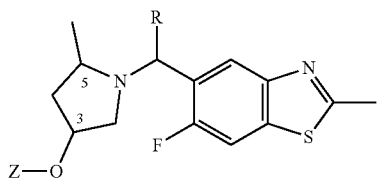

or a pharmaceutically acceptable salt thereof.

3. The compound according to claim 2 wherein R is methyl;
or a pharmaceutically acceptable salt thereof.

4. The compound according to claim 2 wherein R is hydrogen;
or a pharmaceutically acceptable salt thereof.

5. The compound according to claim 3 wherein R is methyl in the (S)-configuration;
or a pharmaceutically acceptable salt thereof.

6. The compound according to claim 3 wherein R is methyl in the (R)-configuration;
or a pharmaceutically acceptable salt thereof.

7. The compound according to claim 1 wherein the compound is:

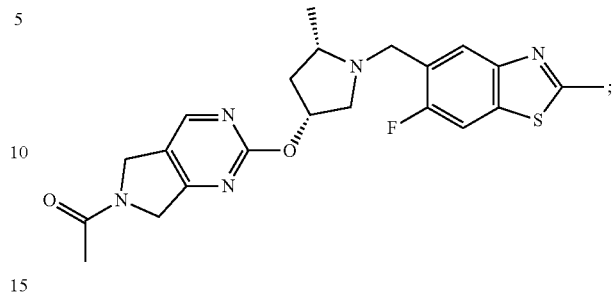

or a pharmaceutically acceptable salt thereof.

8. The compound according to claim 1 wherein the compound is:

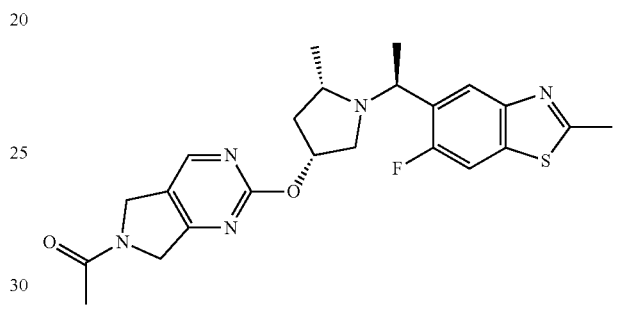

or a pharmaceutically acceptable salt thereof.

9. A method of treating Alzheimer's disease in a patient, comprising administering to a patient in need of such treatment an effective amount of a compound of claim 1, or a pharmaceutically acceptable salt thereof.

10. A method of preventing the progression of mild cognitive impairment to Alzheimer's disease in a patient, comprising administering to a patient in need of such treatment an effective amount of a compound of claim 1, or a pharmaceutically acceptable salt thereof.

11. A method of treating progressive supranuclear palsy in a patient, comprising administering to a patient in need of such treatment an effective amount of a compound of claim 1, or a pharmaceutically acceptable salt thereof.

12. A pharmaceutical composition, comprising a compound or a pharmaceutically acceptable salt thereof according to claim 1 with one or more pharmaceutically acceptable carriers, diluents, or excipients.

* * * * *